(12) United States Patent
Subramaniam

(10) Patent No.: US 6,987,266 B2
(45) Date of Patent: Jan. 17, 2006

(54) STRUCTURE DETERMINATION OF MATERIALS USING ELECTRON MICROSCOPY

(75) Inventor: Sriram Subramaniam, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 24 days.

(21) Appl. No.: 10/475,821

(22) PCT Filed: Apr. 22, 2002

(86) PCT No.: PCT/US02/12605

§ 371 (c)(1),
(2), (4) Date: Aug. 12, 2004

(87) PCT Pub. No.: WO02/086477

PCT Pub. Date: Oct. 31, 2002

(65) Prior Publication Data

US 2005/0056784 A1 Mar. 17, 2005

Related U.S. Application Data

(60) Provisional application No. 60/285,819, filed on Apr. 23, 2001.

(51) Int. Cl.
G01N 1/42 (2006.01)
H01J 37/26 (2006.01)

(52) U.S. Cl. .................. 250/311; 250/306; 250/307; 250/428

(58) Field of Classification Search .............. 250/311, 250/306, 307, 428

See application file for complete search history.

(56) References Cited

U.S. PATENT DOCUMENTS

| 4,865,871 A | * | 9/1989 | Livesey et al. ............ 435/1.3 |
| 5,179,280 A | | 1/1993 | Wang |
| 5,493,865 A | * | 2/1996 | Wohlwend ................ 62/51.1 |
| 6,051,834 A | | 4/2000 | Kakibayashi et al. |
| 6,175,417 B1 | | 1/2001 | Do et al. |

OTHER PUBLICATIONS

Faruqi et al., "CCD detectors in high-resolution biological electron microscopy," Quarterly Reviews of Biophysics, vol. 33, pp. 1–27 (2000).

(Continued)

Primary Examiner—Nikita Wells
(74) Attorney, Agent, or Firm—Merchant & Gould P.C.

(57) ABSTRACT

The invention includes methods for automating acquisition of electron microscopic images. Methods use in the invention include development of search algorithms, including spiral search algorithms for the automated determination of areas suitable for imaging in vitrified specimens at liquid nitrogen temperatures, development of criteria to image areas that meet user-specific needs for the thickness of vitreous ice in which the proteins are embedded, automated setting of key imaging parameters such as extent of defocus and magnification required for recording images, automated assessment of most suitable conditions such as thermal and mechanical stability of specimen stage immediately before recording of the image, recording a "low-dose" image of radiation sensitive biological specimens by carrying out all of the setting and assessment steps on an area immediately adjacent to the area of interest, thereby avoiding pre-exposure of the final imaged area to electrons, creation of a seamless interface to transfer the images recorded on a CCD camera directly to computers capable of processing the recorded images, and carrying out the entire process of data collection from a remote computer either within the network, or connected to the network through a telephone modem from any remote location.

15 Claims, 8 Drawing Sheets

OTHER PUBLICATIONS

Faruqi et al., "Cooled CCD detector with tapered fibre optics for recording electron diffraction patterns," Ultramicroscopy, vol. 74, pp. 235–250 (1999).

Glaeser, "Review: Electron Crystallography: Present Excitement, a Nod to the Past, Anticipating the Future," Journal of Structural Biology, vol. 128, pp. 3–14 (1999).

Oostergetel et al., "Automation of specimen selection and data acquistion for protein electron crystallography," Ultramicroscopy, vol. 74, pp. 47–59 (1998).

Potter et al., "Leginon: a system for fully automated acquisition of 1000 electron micrographs a day," Ultramicroscopy, vol. 77, pp. 153–161 (1999).

Subramaniam et al., "Electron Crystallography of Bacteriorhodopsin with Millisecond Time Resolution," Journal of Structural Biology, vol. 128, pp. 19–25 (1999).

Subramaniam et al., "Molecular mechanism of vectorial proton translocation by bacteriorhodopsin," Nature, vol. 406, pp. 653–657 (Aug. 2000).

Subramaniam et al., "Protein Conformational Changes in the Bacteriorhodopsin Photocycle," J. Mol. Biol., vol. 287, pp. 145–161 (1999).

Fung, et al., "Toward Fully Automated High–Resolution Electron Tomography", Journal of Structural Biology, vol. 116, No. 1, pp. 181–189, Jan., 1996.

Kisseberth, et al., "emScope: A Tool Kit for Control and Automation of a Remote Electron Microscope", Journal of Structural Biology, vol. 120, No. 3, pp. 309–319, Dec. 1997.

Carragher, et al., "Leginon: An Automated System for Acquisition of Images from Vitreous Ice Specimens", Journal of Structural Biology, vol. 132, No. 1, pp. 33–45, Oct. 2000.

* cited by examiner

STRUCTURE DETERMINATION OF MATERIALS USING ELECTRON MICROSCOPY

This application is being filed as a PCT international patent application in the names of The Government of the United States of America, as represented by the Secretary, Department of Health and Human Services (applicant for all countries except the U.S.), and in the name of Sriram Subramaniam, a resident of the U.S. and citizen of India (applicant for U.S. only), on 22 Apr. 2002, designating all countries.

FIELD OF THE INVENTION

The invention relates generally to a method for determining the structure of materials through microscopic imaging. More specifically, the invention relates to automated processes for microscopically imaging materials such as cells, tissue, and macromolecules in which the imaging parameters are automatically determined and set.

BACKGROUND OF THE INVENTION

Over the last three decades, the three-dimensional structures of a variety of biologically interesting macromolecular complexes with helical, icosahedral, octahedral or no symmetry have been determined using images recorded with an electron microscope. High resolution electron microscopic analyses of two-dimensional crystals have in a few instances resulted in structures of proteins with atomic resolution. While analysis of non-crystalline "single particle" suspensions has resulted in the determination of many structures at medium (7 Å–15 Å) resolutions.

Although the last decade has seen considerable improvements in the speed of image analysis, the availability of sufficient numbers of high quality images continues to be the rate limiting step for almost all biological structure determination projects.

An obvious approach to increase the throughput in structure determination efforts is to introduce automated data collection routines that emulate the manual data recording strategies employed by experienced users. Several reports have already appeared in the literature with this aim in mind, and have been pioneered by researchers interested in structure determination using electron tomography, single molecule and helical reconstruction and two-dimensional crystallography. The availability of the partially computerized customized microscopy ("CM") series of microscopes which allowed the construction of efficient hardware and software interfaces to access key microscope controls has been an important element in the success of these efforts. A few recent reports have reported the introduction of significant levels of automation in the data collection process using CM series microscopes, however, these microscopes are no longer manufactured.

For example, Carragher et al., disclose partially automated methods for obtaining electron micrographs in "Leginon: An Automated System for Acquisition of Images from Vitreous Ice Specimens," Journal of Structural Biology, (132, 33–45 (2000)). Similarly, Fung discloses processes for elucidating the three-dimensional architecture of large biological complexes and subcellular organelles in "Toward Fully Automated High-Resolution Electron Tomography," Journal of Structural Biology, (116, 181–189 (1996)). Fung also describes systems that automate the various steps necessary for data collection in tomography. Kisseberth et al. disclose tools that may be used in the control of a remotely situated electron microscope in "emScope: A Tool Kit for Control and Automation of a Remote Electron Microscope", Journal of Structural Biology (120, 309–319 (1997)).

However, much further work is needed in order to eliminate interfaces that decrease image clarity, to allow for more efficient data collection, and to decrease the need for operator interface with the microscope.

SUMMARY OF THE INVENTION

In accordance with one aspect of the invention, there is provided an automated method for the structural determination of a sample using electron microscopy including the steps of defining one or more imaging parameters, selecting one or more sample sites for imaging based upon the imaging parameters, and imaging the one or more sample sites.

In accordance with another aspect of the invention, there is provided an automated method for the structural determination of a sample using electron microscopy including the steps of setting imaging parameters, setting operating conditions of the microscope where the operating conditions are set based on the imaging parameters, and where the microscope includes an electron beam and a microscope stage, locating at least one specific sample site to image, adjusting focus settings, centering the electron beam within the sample site, and taking a picture.

With the advent of computerized microscopes such as the Tecnai series from FEI (Hillsboro, Oreg.), it is now possible to envision general methods for automated data collection that not only completely do away with the requirement of specialized microscope-specific hardware interfaces, but are also accessible to any user via a standardized Windows-based or equivalent desktop interface. The prospect of invoking and monitoring automated data collection on a Tecnai microscope from anywhere in the world by working from a personal computer is a highly attractive one that offers potentially powerful opportunities for high-throughput data collection.

The process of three-dimensional structure determination of a material by electron microscopy can be broken into three distinct stages: (i)specimen preparation, which for example can encompass protein purification and transfer of the sample onto a specimen holder and into the electron microscope, (ii)data collection, which is the process of recording images at the required electron optical settings onto either film or a charge coupled device ("CCD") camera and (iii)image analysis and three-dimensional reconstruction, which computationally processes the information contained in a collection to obtain a three-dimensional structure of the imaged material.

The time necessary to collect the required number of images is an important parameter in all microscopic experiments, but is especially crucial and rate-limiting in high-resolution electron microscopic approaches for biological structure determination. Methods to speed up data collection can be very useful, especially in "single molecule" microscopy of large multi-protein and protein-nucleic acid complexes, where many thousands of individual molecular images have to be averaged to determine the three-dimensional structure.

The claimed invention provides methods for automated low-dose image acquisition procedures on microscopic equipment such as a Tecnai 12 electron microscope (manufactured by FEI, formerly Philips Electron Optics Inc.). In a typical semi-automated session, the user inserts the specimen into the microscope, and quickly selects regions of interest to be imaged. All subsequent steps of image acquisition are carried out automatically to record high resolution images on either film or CCD, at desired defocus values, and under conditions that satisfy user-specified limits for drift rates of the specimen stage. In the fully automated procedure, the initial determination of regions suitable for imaging is also carried out automatically.

The claimed methods also automate all steps following insertion of the specimen in the microscope. These steps can be carried out on a remote personal computer connected to the microscope computer by way of the Internet. Both features are implemented using Windows NT and web-based tools, and in principle, provide tools for automated data collection on any Tecnai microscope by any user from any location.

The invention allows automation of the steps of structure determination of a variety of entities of fundamental interest in biological, medical and veterinary research, with further application to materials science and semiconductor-related materials. Specifically, the invention allows for automated data collection from protein complexes frozen in vitreous ice. Once the specimen is inserted into the microscope, the remaining steps required for data collection can be fully automated.

Knowledge of the three-dimensional structures of biological macromolecules and subcellular assemblies is fundamental both to understanding their function in cells and in rational drug design efforts. The methods of the invention are especially suitable for structural analysis of cellular components that are not easily studied by traditional structural tools such as X-ray crystallography and NMR spectroscopy. The methods may become useful as routine and powerful diagnostic tools in the emerging area of molecular medicine.

DETAILED DESCRIPTION OF THE PREFERRED EMBODIMENTS

Figure 1:
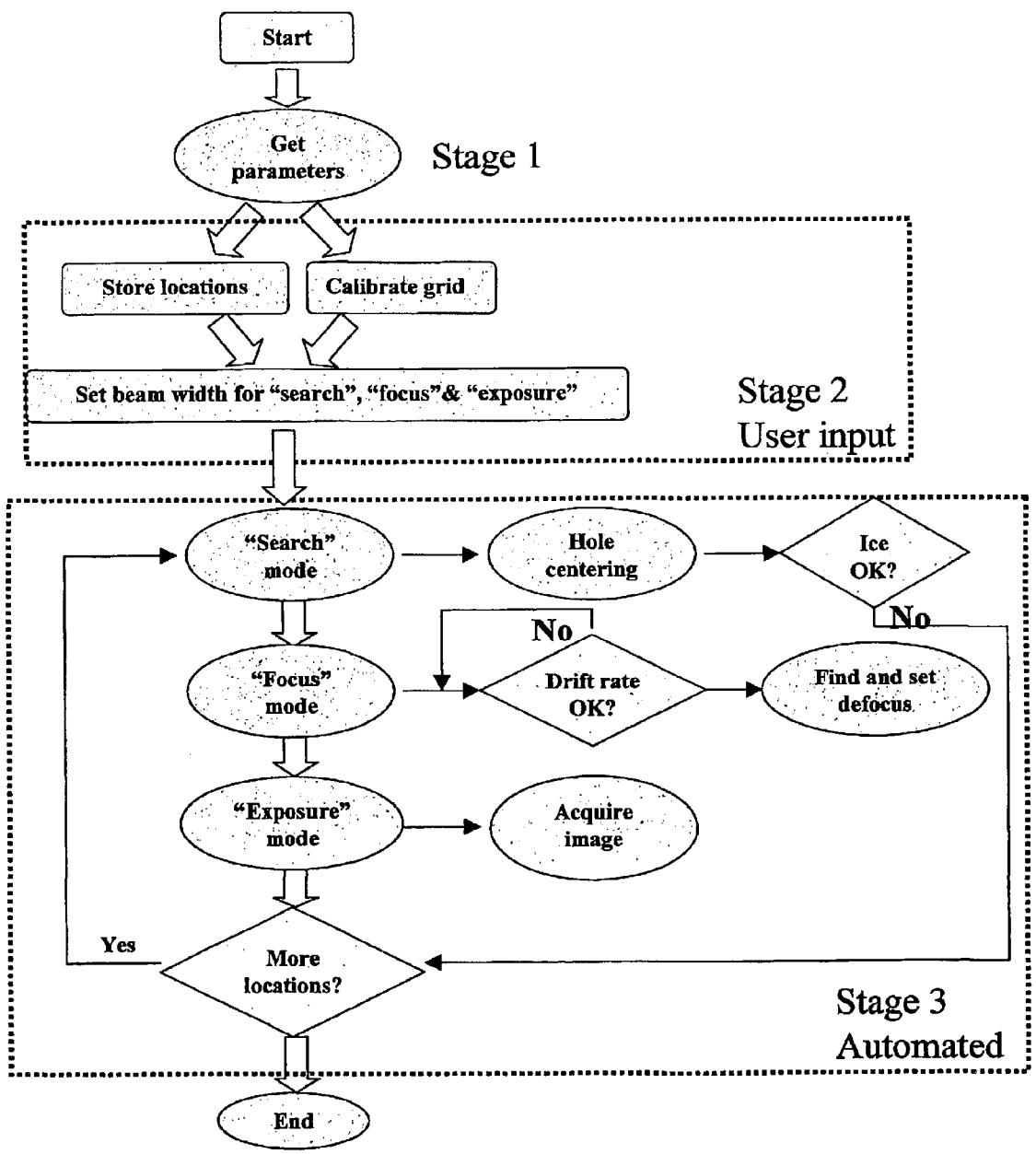
FIG. 1 is a schematic depiction of the steps of automatic data collection in accordance with one embodiment of the invention.

The invention offers automated methods of microscopically imaging materials. Methods of the invention relate specifically to electron microscopes and can encompass varying levels of automation.

Transmission and Scanning Electron Microscopes

Transmission electron microscopes function in much the same way as standard optical microscopes. An optical microscope uses optical lenses to focus light waves by bending them, while an electron microscope uses electromagnetic lenses to focus beams of electrons by bending them. Beams of electrons provide great advantages over beams of light both in control of magnification levels and in the clarity of the image that can be produced. Scanning electron microscopes complement transmission electron microscopes in that they provide a tool to obtain the three dimensional image of the surface of a sample.

Generally, a beam of electrons is produced in an electron microscope by heating a filament. The filament can be made of a variety of metallic materials, including, but not limited to, tungsten or lanthanum hexaboride. This metallic filament functions as the cathode, and when a voltage is applied, the temperature of the filament is increased. An anode, which is positive with respect to the filament, forms a powerful attractive force for electrons. Electrons are attracted from the cathode to the anode, with some passing by the anode to form the electron beam that is used in imaging the sample.

This electron beam is then condensed, and focused onto the sample by using electromagnetic lenses. Scan coils create a magnetic field that can be varied to direct the beam back and forth across the sample in a controlled manner. The same varying voltage that creates the pattern on the sample is applied to a cathode-ray tube. This creates a pattern of light on the surface of the cathode ray tube that is analogous to the one on the sample.

In transmission electron microscopy, thin specimens are used and the structure of the specimen is deduced from the image formed by the electrons collected after their interaction with the specimen. In scanning electron microscopy, the secondary electrons created by interaction of the main beam with the specimen are collected by a secondary detector or a backscatter detector. The collected electrons are then converted into a voltage and amplified. The amplified voltage is then applied to the cathode ray tube and causes the intensity of the light pattern on the surface of the cathode ray tube to change. An image of the topography of the sample consists of numerous spots with varying intensity, as defined by the secondary electrons collected from the sample.

A number of different electron microscopes are commercially available from a variety of companies, examples of such companies include but are not limited to FEI (formerly Philips Electron Optics), JEOL, Hitachi, and Leo (formerly Zeiss). Examples of specific models of commercially available electron microscopes include but are not limited to FEI Tecnai 12, FEI Tecnai F30, and JEOL 1200.

The electron microscopes commercially available today are generally partially computerized. They are typically equipped with a number of fully controllable peripheral devices, such as goniometers, for controlling the position of the sample within the instrument and CCD cameras, for recording and displaying the acquired images.

In microscopes that are partially computer controlled, a software package installed on the microscope computer controls these functions. Often, additional computers are connected externally in order to either control other microscope parameters, such as the beam deflection, or to drive accessories such as CCD cameras mounted on the microscope. In the case of the exemplary Tecnai 12 electron microscope, the microscope computer can run software packages including the Tecnai User Interface ("TUI"), Tecnai Imaging and Analysis ("TIA"), Digital Micrograph and Microsoft® Internet Explorer to provide the user with tools to operate the microscope.

Most software packages, including the exemplary Tecnai 12 software package, support the use of scripts. Scripting allows an experienced user of the instrument to combine computer controlled basic operations of the instrument to create more complex computer controlled operations. For example, the scripting functionality provides the user with commands that mimic some manual manipulations of the microscope. For example, a command could be provided that mimics the action of moving a focus knob on the microscope control panel. Scripting can also be used to combine basic computer controlled operations of the instrument with user created functions that do not make up an original part of the computer controlled instrument.

Methods in accordance with the invention utilize scripts from a number of the programs that are run on the microscope computer. Typically, scripts from TUI, TIA and Digital Micrograph are utilized. The method further envisions using scripts from later versions of similar software. The scripts, even when referred to by name, are referred to and utilized because of their functionality. Therefore, if script names change in later versions of software, the invention can utilize such renamed, but functionally similar scripts.

Samples

Methods of the invention can be used to acquire images of a number of different types of materials or samples. Examples of such samples include, but are not limited to, chemical compounds, metallurgical specimens, semiconductors, drugs, drug complexes, proteins, nucleic acids, including large multi-protein and protein-nucleic acid complexes, cellular organelles, whole cells, and biological tissues. Samples to be imaged with electron microscopy are generally prepared by depositing them on electron microscope grids coated with a carbon film. The carbon film can either be continuous, or perforated. For single molecule microscopic applications, it is especially convenient to use a perforated carbon film containing grids with uniform hole sizes and regular spacing of the holes. Such grids, called Quantifoil® grids, are commercially available. Typical electron microscope grids have holes with diameters of between about 1.2 and 2.0 micrometers ("$\mu$m"). The holes are generally placed in an array on the grid and are spaced about 2 or 4 $\mu$m apart.

It is often desired to maintain the samples at controlled temperatures, generally at very low temperatures. One method of maintaining the samples at low temperatures while carrying out the imaging is through use of cryo-specimen stages. These devices maintain the temperature of the samples and grids at low temperatures by cooling with liquid nitrogen. An example of such a device is a Gatan cryo-specimen stage, model 626 (Pleasanton, Calif.).

The specific techniques used to prepare a sample for imaging depend in great part on the type of sample that is being prepared. One example of a method for preparing protein samples includes freezing the protein molecules in solution. Freezing the protein molecules serves to retain their structure while at the same time reducing radiation damage from the electron beam that can be caused at higher temperatures. One specific method of preparing a protein complex for imaging includes combining the protein with water to form a suspension, depositing a thin film of the suspension on an electron microscope grid, and rapidly freezing the sample/grid at liquid nitrogen temperatures. Examples of systems capable of freezing the sample/grid include liquid ethane ($C_2H_6$) or liquid propane ($C_3H_8$) cooled with liquid nitrogen.

Image Acquisition

Electron microscopes, as mentioned above, are generally controlled in part by a computer that is programmed to acquire the images of the area of interest. However, standard methods of obtaining electron microscope images require the user to locate the exact positions to be imaged (i.e., the center of the hole in the grid), and instruct the computer to acquire the image. The only portion of the data acquisition process that is automated in any substantial way in most microscopes is the sequence of events initiated to acquire an image when the user presses a button on the microscope console. Therefore, the process of acquiring the large number of images necessary to obtain a high resolution three-dimensional structure of the sample typically requires an excessive amount of user time.

FIG. 1 is a schematic flow diagram illustrating methods in accordance with the invention. There are three main stages in the execution of the method. In the first stage, the operator sets up the mode of data collection required by typing in parameters such as magnification, defocus etc. All of these parameters are available as default settings on the user-interface, and generally do not need to be changed, but can be.

In the second stage, there can be at least three available modes to select the locations to be imaged: with a low level of automation, the user selects holes manually at low magnification; with a mid-level of automation, the user selects the squares in a grid, and the computer scans the holes automatically within those selected squares; and with a high level of automation, the hole selection as well as all following steps are accomplished by the computer. At the second stage the user also sets the beam widths to be used for focus setting and for acquiring the image.

The third stage is fully automated and results in the collection of images without any further user intervention. In FIG. 1, the steps requiring user input are shown by rectangles. Steps carried out without user input are shown in diamonds and ovals. The "search", "focus", and "exposure" labels in the automated portion of the script mimic functions usually carried out in a low-dose microscopy session.

The methods offered by the invention encompass varying levels of automation. Three different methods in accordance with the invention will be discussed in further detail: a low level of automation where the user selects the specific holes to be imaged, a mid-level of automation where the user selects the grids containing the prepared sample in the instrument, and a high level of automation where the user need only place the sample in the instrument.

1. Low Level of Automation

In one embodiment, the method of the invention utilizes a low level of automation that begins with the computer requesting the user to select a magnification level for the "search" mode. Next, the computer sets the microscope magnification to the specific value selected for the magnification during "search" mode. Then, the computer requests the user to begin hole selection. Because an automated hole-centering algorithm of the invention can be used, it is not necessary to be very precise in manually centering the selected hole on the viewing screen. The user therefore finds the specific holes to be imaged and stores the general location of these holes. However, the user does not need to locate the exact center of the hole and store that specific location. Generally, the average user requires less than about 10 minutes to select 50 suitable holes on a typical frozen-hydrated specimen grid.

Once the positions of the holes are stored, the user specifies only two other parameters: the width of the beam to be used for recording the image (i.e., in "Exposure" mode), and the width of the beam to be used for estimating and setting the underfocus values at which the image is recorded (i.e. in "Focus" mode).

The computer begins the image acquisition mode by moving the stage holding the sample to the location of the first selected hole. A method of the invention will then apply a hole-centering algorithm. Without use of such an algorithm, the combination of the errors inherent in accurately setting the x-y position of the specimen stage and the spatial errors inherent in selection of a hole generally result in unacceptably large errors for locating the stage precisely when the image is recorded. In a method of the invention, the hole centering algorithm compensates for these errors by using a cross-correlation procedure to measure the displacement of the hole from the absolute center. The beam incident on the specimen is then deflected to match this displacement. The extent of the beam shift involved is sufficiently small so that no significant aberrations are introduced via this procedure.

After the hole to be imaged has been centered, the magnification is changed to the value selected for the "Focus" mode. The focus mode begins by shifting the beam to a neighboring area beyond the circumference of the hole. The drift rate of the specimen stage is monitored by recording successive pairs of images on the CCD camera, and calculating the relative displacement of the peak of the cross-correlation function from the center of the image. Once the drift rate has reached a user-specified level, an automated focus determination procedure is carried out using measurements of the beam-tilt induced displacement. Corrective adjustments may then be made to bring the specimen plane into focus, to minimize the astigmatism, and to set the required underfocus value in preparation for recording an image.

The final step in acquiring the image is the exposure mode. In this step, the beam is shifted back to illuminate the designated hole, the magnification is changed to the value set for the "Exposure" mode and an image is recorded either on film or on the CCD camera as specified by the user. A beam centering routine is carried out at the end of every few exposures to compensate for any slow drifts of the beam over the duration of data collection. It is important to note that by using the above procedure for searching, focusing, and imaging, the material present in the hole is exposed to the beam at only three stages throughout the entire procedure: first when the hole is identified in the Search mode, second when the hole is centered, also in Search mode, and third, when the image is recorded. The accumulated dose on the specimen during the first two stages is <0.1 electrons/$Å^2$), which is approximately 1% of the dose used when the image is recorded.

2. High Level of Automation

In another embodiment of a method of the invention, a high level of automation is utilized. In this embodiment, the best grid squares and suitable holes within those grid squares to be imaged are selected without any action by the user. A subroutine of the program can first establish the principal axes of the square array formed by the grid squares and of the square array formed by the holes. At each grid square, a search is then initiated to sample the full complement of holes within the grid square using a patterned search routine. The search routine may take any variety of patterns across the face of the grid, including spiral, linear, etc., as long as the surface of the grid is covered entirely. Preferably, a spiral search pattern is used.

The specific regions to be imaged are then chosen based on user defined parameters. Generally, programs that make a decision regarding the most suitable regions employ pattern recognition algorithms specific to the type of specimen being imaged. In the case of frozen-hydrated specimens of proteins the decision is based on which holes in each grid square are likely to lead to the highest quality images of the embedded proteins.

The specific parameters used to make this decision and the values that are acceptable will vary depending on a number of factors, including but not limited to the specific samples being imaged, the desired attributes of the images, specific attributes of the electron microscope being used, the chemical composition and buffer conditions present at the time of specimen preparation, and the varying sizes of the molecular components present in the suspension. In manual image acquisition these are factors that advanced users utilize to decide which holes will be imaged.

Examples of relevant factors for a vitreous ice protein sample include but are not limited to ice thickness, ice homogeneity, structure of the periphery of the ice, distribution of ice in the vicinity of the selected, as well as neighboring holes, the apparent gradients in ice thickness from the center of the hole to the periphery, the apparent thickness of ice as related to the overall size of the hole, the sharpness of the edge of the hole, the absence of the contaminating ice crystals in the region being imaged, which ultimately lead to image degradation, the location of the holes with respect to the edges of the grid square, the uniformity of the carbon in the immediate vicinity of the hole, and the fraction of holes in the vicinity which appear suitable for imaging. In general, the criteria used to select a hole are analogous and are dependent on the sample and the method of preparation.

In one embodiment of a method of the invention, the transmittance of electrons through the vitreous ice layer is the criterion used to test whether a hole is suitable for imaging. This is quantified by comparing the average optical density of the CCD image of the center of the hole (recorded under the low magnification conditions specified for the search mode) with the optical density of the CCD image of an empty hole. The empty hole used for the comparison is freshly produced once for every set of four exposures by prolonged irradiation of a hole that has been previously imaged. The creation of a new empty hole as a reference overcomes errors that can arise from slow time-dependent changes in the intensity of the electron beam or variations in background noise of the CCD over the course of an experiment.

To determine the thickness of the ice, it is assumed that the ratio of the two measurements: i.e. optical density of the hole that is being evaluated and the optical density of the empty hole, is related to the thickness of the layer of vitreous ice according to the following equation:

$$t = k \log\left(\frac{I_{hole}}{I_{ice}}\right)$$

where t is the thickness of the ice layer, and k is a proportionality constant. Exact measurements of this constant have not yet been obtained, but empirical analysis from a number of recorded images suggest that it is likely to have a value between about 5,000 and 10,000 Å. Thus a hole with a layer of ice whose optical density is about 7% less than that of an empty hole is likely to correspond to a layer of ice that is ~375 Å thick.

If the estimated ice thickness of the hole falls within a user-specified range, an image is recorded using the protocol already described above in the method with a low level of automation. If the ice thickness is outside of the desired range, the program proceeds to evaluate the next hole using the same procedure. Some rudimentary levels of "intelligence" can be incorporated into this highly automated version of the method to prevent the continued evaluation of holes on a grid square that consistently fall outside the desired ice thickness range.

Once a certain number of the holes in a grid square have been sampled, the procedure is repeated on the next grid square. The number of holes to be sampled in a gridsquare can be specified by the user, or as a default, all holes on a grid square that can be imaged will be.

3. Mid Level of Automation

In a further embodiment, the method of the invention utilizes a mid-level of automation, which is similar to the method above that is highly automated, except that the user has input regarding which squares to search for holes in. Operation at this level of automation can be an effective strategy for experienced users to enhance the throughput of images collected in each session.

User Interface and Remote Operation

Figure 2:
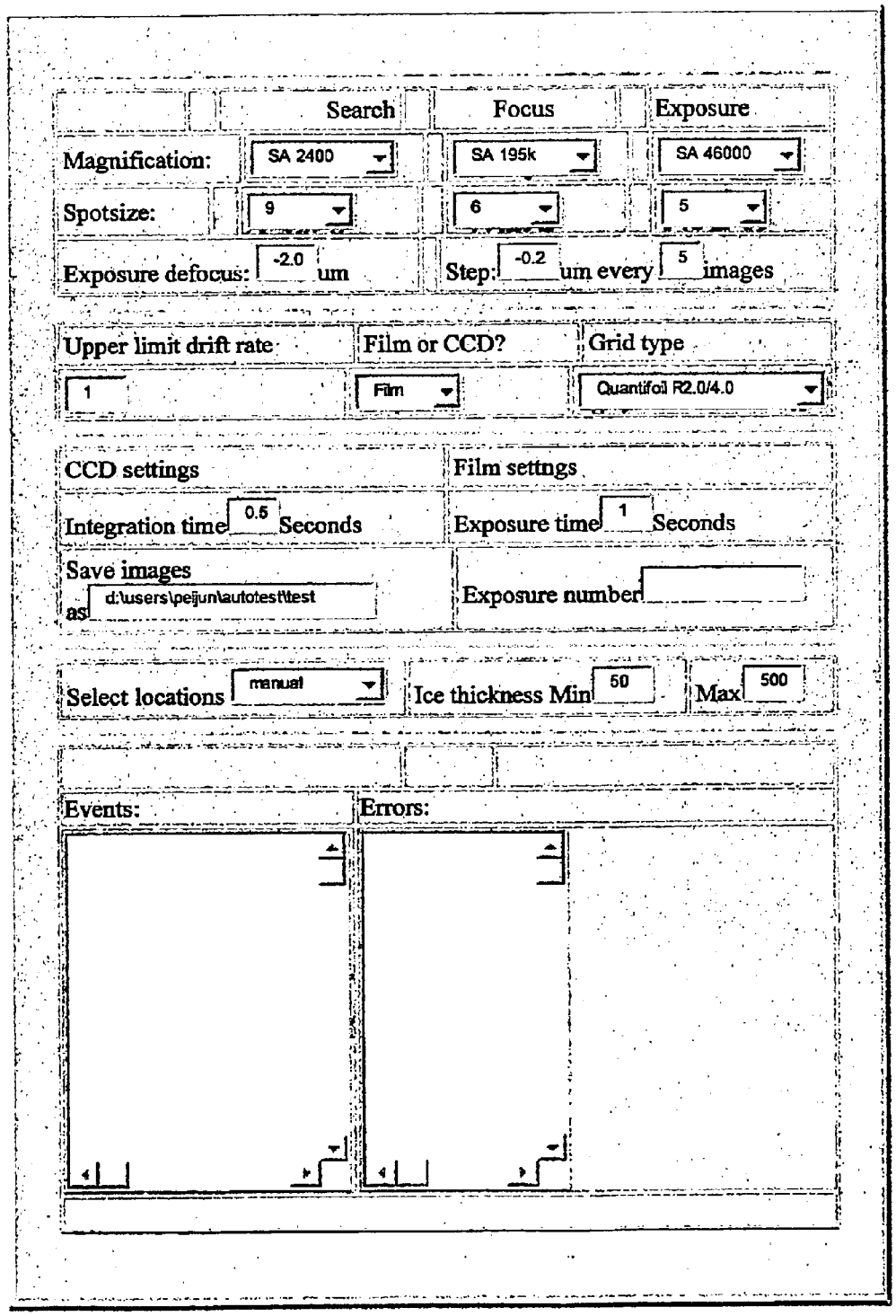
FIG. 2 is a schematic depiction of a user interface of a method in accordance with the invention.

FIG. 2 depicts an example of a software interface of a method of the invention. This interface allows users to define parameters for automated data collection. Default parameters are set (as shown in FIG. 2), and the user may alter the parameters before the automated data collection. The "Events" text field provides detailed information on the steps executed during data collection, while the "Errors" text field reports on errors encountered during an experiment.

Methods of the invention can also be employed using different computer configurations to allow for remote operation via a computer that is not connected to and/or not within the laboratory containing the electron microscope. This can be accomplished by connecting both the computer controlling the electron microscope and the computer for remote control to a local area network (LAN). Alternatively, the computer controlling the microscope can be connected to a separate computer that is then connected to a LAN where the separate computer serves as a gateway computer. Utilization of software such as PC Anywhere (Symantec Corporation, Cupertino, Calif.) then allows remote manipulation of the electron microscope by any computer in the LAN or by a computer on the Internet via a modem connection.

Figure 3:
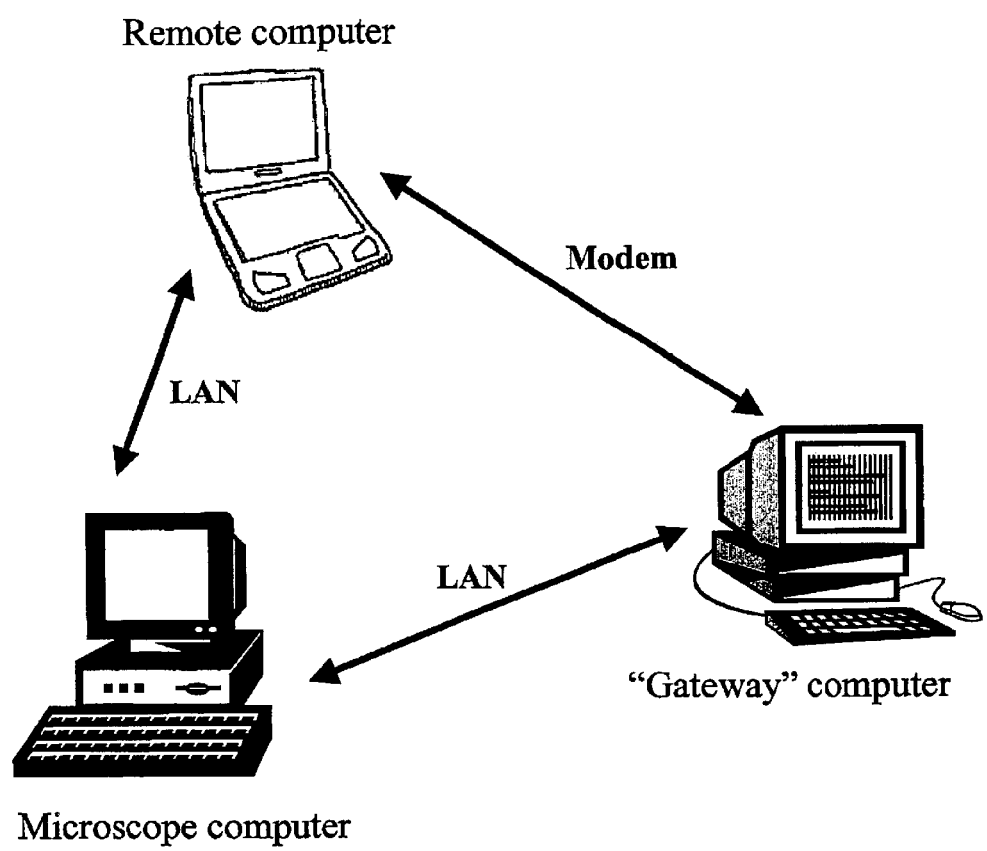
FIG. 3 is a pictorial depiction illustrating the components used for remote operation of an electron microscope in accordance with one embodiment of the invention.

FIG. 3 illustrates one method of setting up remote operation of the microscope. Connections can be made using either a LAN or a modem. The microscope computer runs programs such as the Tecnai user Interface (TUI), Tecnai Imaging and Analysis (TIA), Microsoft® Internet Explore, and PC Anywhere. Scripts use the Javascript/Jscript language, and a web-browser executes the scripts and provides the user interface.

Methods in accordance with the invention may also allow subsequent steps in the acquisition and processing of electron microscope images to be automated. Examples of such post-acquisition steps that could be further automated include but are not limited to transferring the image data to a data analysis program. This specific example would allow for the entire process of data acquisition and analysis to be affected by a user who need only specify a small number of parameters before data acquisition commences. Therefore, when the fully automated process was finished, the user would have the fully acquired, processed and analyzed structural images.

Methods in accordance with the invention would also include those utilizing multi-sample sample holders. This would allow a user to simultaneously load numerous samples, specify the required parameters, and effect data acquisition.

WORKING EXAMPLES

The following examples provide a nonlimiting illustration of certain aspects of the invention.

Example 1

Sample Preparation

This example illustrates one technique of preparing samples for use in a method of the invention.

Samples were prepared using electron microscope Quantifoil® grids with regular arrays of holes, obtained from Quantifoil® Micro Tools GmBH, Germany. Two different size grids were used. The first grid had 1.3 µm diameter holes spaced 2 µm apart (part number R 1.2/1.3). The second had 2 µm diameter holes spaced 4 µm apart Wart number R 2/4). Before use, grids were prepared by being glow-discharged in air for 20 to 30 seconds.

Frozen-hydrated specimens of truncated E2 enzyme (from *B. stearothermophilus*) were then prepared on the previously prepared microscope grid. First, approximately 3 µl of a solution of the truncated E2 enzyme (from *B. stearothermophilus*) containing the icosahedral core of the catalytic domain of pyruvate dehydrogenase was deposited on the grid. Next the grid with the solution deposited thereon was manually blotted with filter paper. Finally, the grid was plunged into a liquid ethane slush, which was at a temperature of −170° C. (−274° F.). The liquid ethane was cooled to that temperature using liquid nitrogen.

The plunge-frozen grids were stored at liquid nitrogen temperatures. In order to maintain the sample at a low temperature during imaging, the samples were transferred into a Gatan cryo specimen stage, Model 626 (Pleasanton, Calif.). The Gatan cryo specimen stage was inserted into the specimen stage holder of the Tecnai microscope in order to maintain the sample at a low temperature during imaging.

Example 2

Microscope and Computer Setup

This example illustrates a specific configuration of hardware that can be used in a method of the invention.

The microscope used in these examples is a Tecnai 12 microscope (FEI Corporation). The Tecnai 12 is equipped with a CompuStage goniometer, and 2K×2K Megascan CCD camera from Gatan (part no. 794.202). The Tecnai 12 is equipped with a computer that can run a number of programs, including the Tecnai User Interface (TUI), Tecnai Imaging and Analysis (TIA), Digital Micrograph and Microsoft Internet Explorer. The computer is controlled with the Windows NT operating system. The Tecnai software platform supports the use of scripts. These scripts can be used to control virtually all microscope parameters that are usually varied by using knobs and buttons present on the microscope. Scripts to control such parameters can be programmed using the Javascript/JScript language and can alternatively be executed and monitored via a web-browser interface.

Example 3

Hardware for Remote Operation

PC Anywhere (Symantec Corporation) was installed on both the computer controlling the microscope and an independent desktop computer. The microscope and desktop computers were then both connected to a LAN. If the operation of the microscope is to be controlled from outside the laboratory, for example from a personal computer at a remote location, the desktop computer served the function of a "gateway" computer. Connection of a remote computer (via either a LAN or a modem connection) to the microscope computer via PC Anywhere enabled manipulation of all functions of the microscope computer, including control of the microscope, from a remote location. When configured in this fashion, the speed at which the display on the remote computer is updated is determined only by the speed of data transmission along the LAN or modem line.

With the web-browser interface (FIG. 3), the user selects values for parameters such as magnification and underfocus at which the search for suitable areas for imaging is carried out, the magnification at which the focus values are measured and set, and the magnification and underfocus values for recording the image. All images can be recorded at the same underfocus value or alternatively, an option is available that allows users to record a series of images, each at a different underfocus value. For routine operation, all of the parameters are available as default settings, eliminating the need for any new input from the user. The "Events" text field reports a variety of useful information that the user can review in order to monitor the progress of data acquisition. The "Errors" text field notes any errors that may be encountered during program execution or in the event of a failure to complete the requested data acquisition process.

Example 4

Subroutine Code

Many detailed functions necessary to carry out high levels of automation can be composed of less complex functions. It is often advantageous to program these less complex functions as subroutines and then combine them to create the overall detailed functions. Many subroutines necessary to carry out the higher functions of automation are given below along with their function.

The specific subroutines given below are to be utilized on a Tecnai 12 electron microscope and utilize the scripts provided therein. Alternatively, subroutines that carry out the same or a similar function that are present in other microscope control systems, or that are created by a user can be utilized.

A. Sets Operating Conditions of the Microscope with Parameters Specified in the Argument of the Function

```
//definition of Conditions
function Conditions(Mag,Intensity,Defocus,SpotSize,ImgShift,
ImgBeamShift){
//ensure that the beam is blanked
MyLowDose.BeamBlanked = eOn;
TimeDelay (0.25);
MyIllum.Intensity = Intensity;      //Intensity
MyProj.Defocus = Defocus;           //Defocus
MyProj.MagnificationIndex = Mag;    //Magnification
MyIllum.SpotSizeIndex = SpotSize;   //Spotsize
MyProj.ImageShift = ImgShift;
MyProj.ImageBeamShift = ImgBeamShift;
}
```

B. Allows User to Store X,Y Locations of Regions Suitable for Imaging

```
//Definition of StoreLocations
function StoreLocations(CaptureType){ //Capture type is film or CCD
MyCamera.MainScreen = 3;           //Put the main screen down
if (CaptureType == 3){             //if film
    var Stock = 300;               //stock is total grid squares
    }
    else {
if (CaptureType == 0){             //if film
    var Stock = MyCamera.Stock;    //stock is whatever is left
}
else{             //if CCD
    var Stock = 50;                //stock is 50
}
}
var i=0;
if (Stock < 1){                    //if the user selected film but there isn't stock left
    return i;                      //the loop will end and zero positions will be
returned
}
else{
    while(Stock > 0){
        if (confirm("You have entered " + i + " positions. You have "+ Stock +" positions
left. Click OK to enter your current position. Click cancel to exit search mode.")){
            var TempPosition = MyStage.Position; //Store position in temporary variable
            if (confirm("X = " + TempPosition.X + " Y = " + TempPosition.Y)){ //confirm
that position is correct
                i=i+1;
                Positions[i] = TempPosition;     //store position into global variable
                Stock = Stock - 1;               //reduce number of pictures available to user
                }
            }
        else{
          Stock = 0;                //reducing stock to 0 exits the loop
          }
        }                           //while loop ends
    return i;                       //return number of positions entered
    }                               //else close
}
```

C. Sends Microscope Stage to Specified Location

```
//Definition of GoToLocation
function GoToLocation(i){         //moves stage to position
var Pos = Positions[i];           //gets position from array
MyStage.GoTo(Pos,3);              //moves to that position,
                                    along XY axis
```

-continued

```
message="\n Goto Position " + i;
DisplayEvent(message);
}
```

D. Centers Electron Beam on Screen

```
//Definition of BeamCenter
function BeamCenter( ){                          //centers the beam
var Status = "true";
MyCamera.MainScreen = 3;                         //puts the main screen down
var ScrCurrent = MyCamera.ScreenCurrent;
var threshold = 1.25*0.0000000001;               //threshhold current value
var OrigInt = MyIllum.Intensity;                 //stores original conditions
var OrigSpot = MyIllum.SpotSizeIndex;
while ((ScrCurrent < threshold) && (MyIllum.Intensity < 0.45)){ //if screen current
below threshold, first tries to increase intensity, 0.45 is the exposure int limit
      MyIllum.Intensity = MyIllum.Intensity + 0.01;
      ScrCurrent = MyCamera.ScreenCurrent;
}
while ((ScrCurrent < threshold) && (MyIllum.SpotSizeIndex > 3)){
      MyLowDose.BeamBlanked = eOn;
      MyIllum.SpotSizeIndex = 3;
      TimeDelay(1.0);
      MyLowDose.BeamBlanked = eOff;
      TimeDelay(0.5);
      ScrCurrent = MyCamera.ScreenCurrent;
}
if (ScrCurrent >= threshold) {
var XP = FindEdge(0,1,0);                        //finds right edge
TimeDelay(0.5);                                  //delay makes it work better?
var XN = FindEdge(0,-1,0);                       //finds left edge
TimeDelay(0.5);
var YP = FindEdge(0,0,1);                        //finds top edge
TimeDelay(0.5);
var YN = FindEdge(0,0,-1);                       //finds bottom edge
var BeamShift = MyIllum.Shift;
BeamShift.X = BeamShift.X + (XP + XN)/2;         //center in x
BeamShift.Y = BeamShift.Y + (YP + YN)/2;         //center in y
MyIllum.Shift = BeamShift;                       //shift beam to center
if ((MyIllum.Intensity!=OrigInt)||(MyIllum.SpotSizeIndex != OrigSpot)){
MyLowDose.BeamBlanked = eOn;
MyIllum.Intensity = OrigInt;
MyIllum.SpotSizeIndex = OrigSpot;
TimeDelay(1.0);
MyLowDose.BeamBlanked = eOff;
TimeDelay(0.5);
BeamCenter( ); //sometimes beam shifts when spot size changes due to bad
alignment.
}
}
else {
//just takes the previous beam center
MyIllum.Intensity = OrigInt;
MyIllum.SpotSizeIndex = OrigSpot;
message = "\n Beam intensity is too low, can not perform BeamCenter( )!!!";
DisplayEvent(message);
Status = "false";
return Status;
}
}
```

E. Locates Edge of Screen when the Electron Beam Disappears

```
//Definition of FindEdge
function FindEdge(value,Xdir,Ydir){
var initial = MyIllum.Shift;                //stores original shift
var sig;
var step = 0.000000005;                     //step size
var RefScreenCurrent = MyCamera.ScreenCurrent;//screen current that others will be
compared to
var ScreenCurrent = RefScreenCurrent;       //transient screen current
var BeamShift = MyIllum.Shift;
while (ScreenCurrent > 0.5*RefScreenCurrent){       //step1 - coarse adjustment
    BeamShift = MyIllum.Shift               //initialize beam shift
    BeamShift.X = BeamShift.X + Xdir*step;  //shift in X and Y separately
    BeamShift.Y = BeamShift.Y + Ydir*step;
    MyIllum.Shift = BeamShift;                  //executes shift
    value = value + Xdir*step + Ydir*step;      //stores value
    ScreenCurrent = MyCamera.ScreenCurrent;         //registers screen current to find
how close it is to off the screen
}
step = 0.0000000025;                        //step2
while (ScreenCurrent > 0.25*RefScreenCurrent){
    BeamShift = MyIllum.Shift                   //initialize beam shift
    BeamShift.X = BeamShift.X + Xdir*step;      //shift in X and Y separately
    BeamShift.Y = BeamShift.Y + Ydir*step;
    MyIllum.Shift = BeamShift;                  //executes shift
    value = value + Xdir*step + Ydir*step;      //stores value
    ScreenCurrent = MyCamera.ScreenCurrent;         //registers screen current to find
how close it is to off the screen
}
step = 0.000000001;                         //step3
while (ScreenCurrent > 0.1*RefScreenCurrent){
    BeamShift = MyIllum.Shift
    BeamShift.X = BeamShift.X + Xdir*step;
    BeamShift.Y = BeamShift.Y + Ydir*step;
    MyIllum.Shift = BeamShift;
    value = value + Xdir*step + Ydir*step;
    ScreenCurrent = MyCamera.ScreenCurrent;
}
MyIllum.Shift = initial;                    //returns it to original shift
return value;
}
```

F. Determines the Drift Rate of the Microscope Stage

```
//Definition of FindDrift
function FindDrift(MaxDriftRate){
var status = "true";
var rate = MaxDriftRate + 1;                //initialize rate
var NumMeasurement = 0;
while (rate > MaxDriftRate){                //while drift is to much
//stop measuring after 20 measurements, and skip the location
        if (++NumMeasurement > 20){
        message = "\n!!!Drift measurement stoped";
        DisplayEvent(message);
        status = "false";break;}
    TakeACCDPicture("drifta");              //take first picture
    var drifta = FindTime( );               //store first time
    TakeACCDPicture("driftb");              //take second picture
    var driftb = FindTime( );               //store second time
    var DriftDisplacement = FindDisplacement("drifta","driftb"); //calls displacement
function
    var DriftDisplacementX = DriftDisplacement.X*10000000000; //convert to
Angstroms
    var DriftDisplacementY = DriftDisplacement.Y*10000000000; //convert to
Angstroms
    var DriftDist = Math.sqrt(DriftDisplacementX * DriftDisplacementX +
DriftDisplacementY * DriftDisplacementY); //calculates drift distance
    var rate = DriftDist/(driftb - drifta); //calculates drift rate
```

-continued
```
message="\n Drift rate= "+ rate;
DisplayEvent(message);
}
return status;
}
```

G. Determines the Spatial Shift Between Two Images

```
//Definition of FindDisplacement
function FindDisplacement(image1,image2){
//FileDir = document.MainForm.FileDir.value;
var Window1 = MyTia.OpenDisplayWindow(FileDir + image1 + ".emi"); //open first
image
Window1.Name = "Window1";
var image1 = MyTia.FindDisplayObject("Window1/CCD Image Display/CCD
Image"); //store image data in a variable
var Window2 = MyTia.OpenDisplayWindow(FileDir + image2 + ".emi"); //open
second image
Window2.Name = "Window2";
var image2 = MyTia.FindDisplayObject("Window2/CCD Image Display/CCD
Image"); //store image data in a variable
image2.Data = MyMath.CrossCorrelation(image1, image2)   //cross-correlate
the images
var Max1 = MyMath.PositionMax(image2.Data); //store the position of the maximum
MyTia.SaveDisplayWindow("Window2",FileDir +"CCF" + image1 + ".emi");
MyTia.CloseDisplayWindow("Window1");
MyTia.CloseDisplayWindow("Window2");
return Max1; //return value of maximum - indicative of displacement
}
```

H. Takes a Low Dose Picture on Photographic Film

```
//Definition of TakeALDFilmPicture
function TakeALDFilmPicture( ){
var ExpTime = document.MainForm.ExposureTime.value; //exposure time
in sec
MyLowDose.PlateExposureTime = ExpTime;
MyLowDose.WaitTime = 5;
if (MyLowDose.ExposeStatus != eInExpose){
        MyLowDose.LowDoseExpose = eStart;
        TimeDelay (0.5);
        while (MyLowDose.ExposeStatus == eInExpose){
        LDExposeStatusChanged( );}}
else{   MyLowDose.LowDoseExpose = eAbort;
        TimeDelay (0.5);
        TakeALDFilmPicture( );}
//go back to LD exposure mode and blank the beam, because it auto
switch to LD focus mode
MyLowDose.BeamBlanked = eOn;
ExposureMode( );
}
//-------------------------------------------
```

I. Takes a Picture on Film

```
//Definition of TakeAFilmPicture
function TakeAFilmPicture(i){        //takes a picture on film
var ExpTime = document.MainForm.ExposureTime.value; //exposure
                                                     time in sec
    MyCamera.MainScreen = 2;
MyCamera.ManualExposure = 1;         //true for manual
                                       exposure
MyCamera.ManualExposureTime=ExpTime;
    PVP( );
    BeamBlank(0);
    MyCamera.TakeExposure( );
}
```

J. Checks to See if PVP (Prevacuum Pump) is Running

```
//Definition of PVP
function PVP( ){                     //checks to see if PVP is
                                       running
var Running = MyVacuum.PVPRunning;
while (Running = = 1){
    Running = MyVacuum.PVPRunning;   //while PVP is running,
                                       executes the loop
}
}
```

K. Takes a Picture on CCD

```
//Definition of TakeACCDPicture
function TakeACCDPicture(i){    //takes a CCD picture and saves it as the
MyCamera.MainScreen = 2; //puts the main screen up
MyCCD.CameraInserted = true;
//open the necessary files in TIA
if (Mode=="focus"){
MyTia.OpenDisplayWindow("c:/users/peijun/setups/focusacquisition.emi");
MyCCD.IntegrationTime = 0.2;
}
else {
MyTia.OpenDisplayWindow("c:/users/peijun/setups/acquisition.emi");
MyCCD.IntegrationTime = document.MainForm.IntegTime.value;
}
//Single acquisition set-up
MyCCD.AcquireMode(1);
MyTia.ActiveDisplayWindow( ).Name = "Window";
var state = MyAcqMan.CanStart( );
var counter = 1;
while (state == 0){
    state = MyAcqMan.CanStart( );
    counter = counter + 1;
    if (counter==50){
        break;
    }
}
//checks PVP
PVP( );
//unblanks the beam
MyLowDose.BeamBlanked = eOff;
TimeDelay(0.5);
//acquires an image
MyAcqMan.Acquire( );
//Stops acquiring if there is a problem
var State = MyTia.AcquisitionManager( ).IsAcquiring( );
if (State == true){
    MyAcqMan.Stop( );
}
//save file
var filename = FileDir + i + ".emi";
//close out of TIA windows
MyTia.SaveDisplayWindow("Window", filename);
MyTia.CloseDisplayWindow("Window");
}
```

L. Finds the Absolute Time

```
//Definition of FindTime
function FindTime( ){         //returns the absolute time
var today = new Date( );
var hours = today.getHours( );
var minutes = today.getMinutes( );
var seconds = today.getSeconds( );
var secondstime = seconds + 60*minutes + 60*60*hours;
return secondstime;         //gives the time in seconds
}
//Definition of FindTime2
function FindTime2( ){        //returns the absolute time
var today = new Date( );
var hours = today.getHours( );
var minutes = today.getMinutes( );
var minutestime = minutes + 60*hours;
return minutestime;         //gives the time in seconds
}
```

M. Sets Waiting Time Between Commands

```
//Definition of TimeDelayNew
function TimeDelayNew(sec){ //doesn't have consistent time
var GridType;
var count = sec*6000;
var i=1;
while(i<count) {
GridType = document.MainForm.GridType.selectedIndex;
i=i+1;
}
}
//Definition of TimeDelay
function TimeDelay(sec){
var count = sec*2000000;
var i=1;
for (i=1;i<count;i=i+1){ }
}
```

N. Carries Out Automated Measurement of Focus and Sets to Desired Value

```
//Definition of Autofocus
function AutoFocus( ){
MyIllum.DFMode = 1;
//switch to dark field mode, other conditions
ChangeConditions( );
MyCamera.MainScreen = 2;
var BeamTiltA = 0.0005;
BackToZero( );
//Take untilted image
TakeACCDPicture("image1");
//Tilt in the X-direction
InduceBeamTilt(BeamTiltA,1,0);
TakeACCDPicture("image2");
BackToZero( );
//Tilt in the Y direction
InduceBeamTilt(BeamTiltA,0,1);
TakeACCDPicture("image3");
BackToZero( );
//determine the image displacement for X and Y direction images (with respect to the
initial image) using TIA
var ImageDisplacementXP = FindDisplacement("image1","image2");
var ImageDisplacementYP = FindDisplacement("image1","image3");
//find defocus using methods and equations found in Koster
var DefocusAndAstig =
FindAstigAndDefocus(ImageDisplacementXP,ImageDisplacementYP,BeamTiltA);
//adjust defocus
Adjustment(DefocusAndAstig, AutoFocusSet);
//return to bright field mode
MyIllum.DFMode = 1;
}
//-----------------------------------------------------------
//Definition of Autofocus2
function AutoFocus2( ){
var status = "true";
MyIllum.DFMode = 1;
//switch to dark field mode, other conditions
ChangeConditions( );
MyCamera.MainScreen = 2;
var BeamTiltA = 0.0005;
BackToZero( );
//Take untilted image
TakeACCDPicture("image1");
//Tilt in the X-direction
InduceBeamTilt(BeamTiltA,1,0);
TakeACCDPicture("image2");
BackToZero( );
//Tilt in the Y direction
InduceBeamTilt(BeamTiltA,0,1);
TakeACCDPicture("image3");
BackToZero( );
//determine the image displacement for X and Y direction images (with respect to the
initial image) using TIA
var ImageDisplacementXP = FindDisplacement("image1","image2");
var ImageDisplacementYP = FindDisplacement("image1","image3");
//find defocus using methods and equations found in Koster
var DefocusAndAstig =
FindAstigAndDefocus(ImageDisplacementXP,ImageDisplacementYP,BeamTiltA);
//return to bright field mode
MyIllum.DFMode = 1;
var Difference = DefocusAndAstig[1] + AutoFocusSet;
    //DefocusAndAstig[1] is "+"
if ( Math.abs(Difference )> 0.00000080 ) { //if 2nd focus volue off greater than
0.5um, return status false
message = "\n Can not find focus!!!";
DisplayEvent(message);
status = "false";
}
Adjustment(DefocusAndAstig,0);
return status;
}
//Changes the conditions to those required for the execution of the program
function ChangeConditions( ){
```

```
//switch to dark field
MyIllum.DFMode = 2;
BackToZero( );
}
//----------------------------------------------------------
```

O. Induces a Beam Tilt of a Specified Number of Degrees

```
//Definition of InduceBeamTilt
//induces a beam tilt of a specified number of degrees
function InduceBeamTilt(Angle,XDir,YDir){
    var BeamTiltVector = MyIllum.Tilt;
    BeamTiltVector.X = BeamTiltVector.X + XDir*Angle;
    BeamTiltVector.Y = BeamTiltVector.Y + YDir*Angle;
    MyIllum.Tilt = BeamTiltVector;
    }
//----------------------------------------------------------
```

P. Finds Defocus Using Methods and Equations

```
//Definition of FindAstigAndDefocus
//finds defocus using methods and equations found in Koster
function FindAstigAndDefocus(disp1,disp2,Angle){
    var Defocus = (disp1.X + disp2.Y)/2/Angle;
    var Phi = 0.5*Math.atan((Math.abs(disp1.Y) +
    Math.abs(disp2.X))/(disp1.X −
    disp2.Y));
    var Astig = (Math.abs(disp1.Y) +
    Math.abs(disp2.X))/Angle/Math.sin(2*Phi);
    var DefocusAPhi = new Array( );
    DefocusAPhi[1] = Defocus;
    DefocusAPhi[2] = Astig;
    DefocusAPhi[3] = Phi;
    //message="find defocus=
    "+Defocus+"---"+"Astig="+Astig+"---"+"Phi="+Phi;
    //DisplayEvent(message);
    return DefocusAPhi;
    }
//----------------------------------------------------------
```

Q. Adjusts Focus Settings

```
//Definition of Adjustment
function Adjustment(DefocusAndAstig,DefocusSet){
    MyProj.Defocus = MyProj.Defocus + DefocusAndAstig[1]; //focus
    adjuest back
    MyProj.ResetDefocus( );
    MyProj.Defocus = DefocusSet;
    }
```

R. Takes a Low Magnification CCD Picture, Saves it, and Returns the Average Intensity of the Image

```
//Definition of TakeACCDPictureLow
function TakeACCDPictureLow(i, size ){   //takes a low mag CCD picture
and saves
it
var IniIntensity = MyIllum.Intensity;
MyCamera.MainScreen = 2; //puts the main screen up
MyCCD.CameraInserted = true;
//open the necessary files in TIA
if (size = = "full"){
    MyIllum.Intensity = 0.6;   //Intensity
    MyTia.OpenDisplayWindow("c:/users/peijun/setups/fullsizelow.emi");
}
else{
    MyTia.OpenDisplayWindow("c:/users/peijun/setups/"+SetUpFile+".emi");
}
//Single acquisition set-up
MyCCD.AcquireMode(1);
MyCCD.IntegrationTime = 0.5;
MyTia.ActiveDisplayWindow( ).Name = "Window";
var state = MyAcqMan.CanStart( );
var counter = 1;
while (state = = 0){
    state = MyAcqMan.CanStart( );
    counter = counter + 1;
    if(counter= =50){
        break;
    }
}
//ensure that the beam is unblanked
MyLowDose.BeamBlanked = eOff;
TimeDelay(0.5);
//acquires an image
    MyAcqMan.Acquire( );
//Stops acquiring if there is a problem
var State = MyTia.AcquisitionManager( ).IsAcquiring( );
if (State = = true){
    MyAcqMan.Stop( );
}
//save file
var filename = FileDir + i +".emi";
MyTia.SaveDisplayWindow("Window", filename);
MyLowDose.BeamBlanked = eOn;
//get sum int
var image = MyTia.FindDisplayObject("Window/CCD Image
Display/CCD Image");
var SumInt = MyMath.Sum(image.Data);
//close out of TIA windows
MyTia.CloseDisplayWindow("Window");
MyIllum.Intensity = IniIntensity;      //get back to initial
                                        intensity if there is a
change
return SumInt;
}
//----------------------------------------------------------
```

S. Sends Out the Average Intensity of Central 40×40 Pixels

```
//Definition of GetAvgPixInt
// send out the avg Int of central 40×40 pixels
function GetAvgPixInt(image){
    var filename = FileDir + image +".emi";
    var Window1 = MyTia.OpenDisplayWindow(filename);
    Window1.Name = "Window1";
    var Window2 = MyTia.OpenDisplayWindow(filename);
    Window2.Name = "Window2";
    var image1 = MyTia.FindDisplayObject("Window1/CCD Image
    Display/CCD
    Image");
    var image2 = MyTia.FindDisplayObject("Window2/CCD Image
    Display/CCD
    Image");
    image2.Data = image1.Data.PixelSelection(ImageSize/2−
    20,ImageSize/2−20,
    ImageSize/2+20, ImageSize/2+20);
```

-continued

```
    var AvgPixInt = MyMath.Sum(image2.Data)/1600;   //average
    intensity of a pixel for
    20x20 area
    alert ("average Int of 40x40 pixels= "+AvgPixInt);
    MyTia.SaveDisplayWindow("Window2", FileDir+"area.emi");
    MyTia.CloseDisplayWindow("Window1");
    MyTia.CloseDisplayWindow("Window2");
    return AvgPixInt;
    }
//--------------------------------------------------
```

T. Finds the Center of the Hole

```
//Definition of FindHoleCenter
function FindHoleCenter( ){
    TakeACCDPictureLow("hole", "small");       // Take a low mag
                                               ccd image in
search mode
    var HoleCenterShift = FindDisplacement("hole", "refhole"); //calls
    displacement
    return HoleCenterShift;
}
//--------------------------------------------------
```

U. Estimates the Thickness of the Ice in a Hole

```
// Definition of FindIce
function FindIce( ){
var Window1 = MyTia.OpenDisplayWindow(FileDir + "hole.emi");//open
low mag
image
Window1.Name = "Window1";
var image1 = MyTia.FindDisplayObject("Window1/CCD Image
Display/CCD
Image"); ;
image1.Data = image1.Data.PixelSelection(ImageSize/2-
10,ImageSize/2-10,
ImageSize/2+10, ImageSize/2+10);
var AvgIntIce = MyMath.Sum(image1.Data)/400; //average intensity of
a pixel for
20x20 area
if(Math.log10(10*AvgIntIce/AvgIntHole)>=0.85 &&
MyMath.log10(10*AvgIntIce/AvgIntHole)<=0.95){
var IceStatus = "true";
}
else var IceStatus = "false";
MyTia.CloseDisplayWindow("Window1");
return IceStatus;
}
//--------------------------------------------------
```

V. Resets Microscope Conditions

```
// Definition of OnReset
function OnReset( ){
    if (MyLowDose.LowDoseActive = = eOn){
        MyLowDose.BeamBlanked = eOff;   //ensure that the beam
        is unblanked
        ExposureMode( );}          //go to exposure mode
    else {
        BeamBlank(0);} //beam unblanked
        MyProj.MagnificationIndex = 20;   //Magnification=2400x
        MyIllum.Intensity = 0.6;       //Intensity
        MyProj.Defocus = 0.0000;              //Defocus, 20um
        MyIllum.SpotSizeIndex = 8;   //Spotsize
        MyProj.ImageShift.X = 0;
        MyProj.ImageShift.Y = 0;
        MyProj.ImageBeamShift.X = 0;
        MyProj.ImageBeamShift.Y = 0;
        MyIllum.Shift.X=0;
        MyIllum.Shift.Y=0;
    }
//--------------------------------------------------
```

W. Output of X,Y Positions of Locations

```
// Definition of SavePositions
function SavePositions(number){
    if((_result==null)||(_result.closed)) {
        _result = window.open("", "consol", "width=600, height=300,
        resizable, scrollbars");
        _result.document.open ("text/plain");
    }
    var msg = "\n Stage Positions:";
    _result.document.writeln(msg);
    var i=1;
    for (i=1;i<=number;i=i+1){
        var TempPos = Positions[i];
        TempPos.X=TempPos.X*1000000;
        TempPos.Y=TempPos.Y*1000000;
        msg = TempPos.X +", "+TempPos.Y;
        _result.document.writeln(msg);
    }
}
//--------------------------------------------------
```

X. Determines the Displacement of a Hole

```
// Definition of FindShift
function FindShift(i){
    var RealHoleShift = FindDisplacement(i, "ref"); //calls displacement
// alert ("Hole center shift="+ RealHoleShift.X+", "+RealHoleShift.Y);
    return RealHoleShift;
}
//--------------------------------------------------
```

Y. Determines the Angle Between CCD Axis Set by the Coils on the Microscope

```
    // Definition of GetAlpha
    function GetAlpha( ){
    TakeACCDPictureLow("alpha0", "small");
    AlphaBeamShift(1);
    TakeACCDPictureLow("alpha1", "small");
    AlphaBeamShift(-1);
    var ShiftDisplacement = FindDisplacement("alpha1","alpha0");
    var ratio=ShiftDisplacement.X/ShiftDisplacement.Y;
    var angle=Math.atan(ratio);
    var angle1=180*angle/3.14;
    message="\n Alpha angle = " + angle1+" degree";
    DisplayEvent(message);
    return angle;
    }
//--------------------------------------------------
```

Z. Exposes the Area Used for Focus Determination for Specified Value of Time without Taking a CCD Picture

```
// Definition of CCDExpose
function CCDExpose(time){ //expose the focus area for "time" sec
without take ccd
picture
```

-continued

```
//var FileDir = document.MainForm.FileDir.value;
MyCamera.MainScreen = 3; //puts the main screen down
//open the necessary files in TIA
MyTia.OpenDisplayWindow("c:/users/peijun/setups/acquisition.emi");
MyCCD.IntegrationTime=time;
//Single acquisition set-up
MyCCD.AcquireMode(1);
MyTia.ActiveDisplayWindow( ).Name = "Window";
var state = MyAcqMan.CanStart( );
var counter = 1;
while (state == 0){
    state = MyAcqMan.CanStart( );
    counter = counter + 1;
    if (counter= =50){
        break;
    }
}
//ensure that the beam is unblanked
MyLowDose.BeamBlanked = eOff;
//acquires an image
MyAcqMan.Acquire( );
//Stops acquiring if there is a problem
var State = MyTia.AcquisitionManager( ).IsAcquiring( );
if (State = = true){
    MyAcqMan.Stop( );
}
//save file
var filename = FileDir + "test.emi";
//close out of TIA windows
MyTia.SaveDisplayWindow("Window", filename);
MyTia.CloseDisplayWindow("Window");
}
//---------------------------------------------------
```

A2. Irradiates Ice in Hole Long Enough to Melt a Hole

```
// Definition of BurnAHole
function BurnAHole(BeamInt){
var InitialIntensity = MyIllum.Intensity;
MyIllum.Intensity = BeamInt;
TimeDelay(1.5);
var InitialCurrent = MyCamera.ScreenCurrent;
var count=1;
while ((MyCamera.ScreenCurrent < 1.10 * InitialCurrent)&& count<=3 ){
//need to
check the ratio-------------------->
CCDExpose(20);
//alert("Count="+count);
//alert ("InitialCurrent="+InitialCurrent+",
current="+MyCamera.ScreenCurrent);
count=count+1;
}
CCDExpose(30);    //after current starts to change, take 30 sec
to burn a
hole
MyIllum.Intensity = InitialIntensity;
MyLowDose.BeamBlanked = eOn;
}
//---------------------------------------------------
```

B2. Searches for Locations to Image

```
// Definition of SearchMode
function SearchMode( ){
if (MyLowDose.LowDoseState != eSearch){
    LDState = "false";
    MyLowDose.LowDoseState = eSearch;
    while (LDState = = "false"){
        LowDoseStateChanged( );}}
}
//---------------------------------------------------
```

C2. Acquires Images of Locations

```
// Definition of ExposureMode
function ExposureMode( ){
if (MyLowDose.LowDoseState != eExposure){
    LDState = "false";
    MyLowDose.LowDoseState = eExposure;
    while (LDState == "false"){
        LowDoseStateChanged( );}}
}
//---------------------------------------------------
```

D2. Focuses the Beam

```
// Definition of FocusMode
function FocusMode( ){
if (MyLowDose.LowDoseState != eFocus1){
    LDState = "false";
    MyLowDose.LowDoseState = eFocus1;
    while (LDState = ="false"){
        LowDoseStateChanged( );}}
}
//---------------------------------------------------
```

E2. Obtains Spacing of Grid Bars

```
// Definition of GetGridPar
function GetGridPar( ){
alert("Prepare grid square parameters, require 3 squares in a row.
\n switch to a lower
mag, if necessary");
alert ("go to corner of a square");
var PosStartA = MyStage.Position;
alert("walk 3 squares in one direction, and to the same corner");
var PosEndA = MyStage.Position;
var Ax=(PosEndA.X-PosStartA.X)/3;
var Ay=(PosEndA.Y-PosStartA.Y)/3;
var theta = Math.atan2(Ay,Ax)*180/3.14;
var distA=Math.sqrt(Ax*Ax+Ay*Ay);
//alert("theta="+theta+", Dist="+distA);
alert ("go to corner of a square");
var PosStartB = MyStage.Position;
alert("walk 3 squares in another direction");
var PosEndB = MyStage.Position;
var Bx=(PosEndB.X-PosStartB.X)/3;
var By=(PosEndB.Y-PosStartB.Y)/3;
var theta2 = Math.atan2(By,Bx)*180/3.14;
var distB=Math.sqrt(Bx*Bx+By*By);
alert("theta="+theta2+", Dist="+distB);
GridPar[1]=Ax;
GridPar[2]=Ay;
GridPar[3]=Bx;
GridPar[4]=By;
}
//---------------------------------------------------
```

F2. Obtains Spacing of Holes

```
//Definition of GetHolePar
function GetHolePar( ){
alert("Prepare hole parameters, \n requares 5 holes in each direction");
alert ("go to a hole center");
var PosStartA = MyStage.Position;
alert("walk 5 holes in one direction, and to the center");
var PosEndA = MyStage.Position;
var Ax=(PosEndA.X-PosStartA.X)/5;
var Ay=(PosEndA.Y-PosStartA.Y)/5;
var theta = Math.atan2(Ay,Ax)*180/3.14;
var distA=Math.sqrt(Ax*Ax+Ay*Ay);
```

-continued

```
//alert("theta="+theta+", Dist="+distA);
alert ("go to a hole center");
var PosStartB = MyStage.Position;
alert("walk 5 squares in another direction");
var PosEndB = MyStage.Position;
var Bx=(PosEndB.X-PosStartB.X)/5;
var By=(PosEndB.Y-PosStartB.Y)/5;
var theta2 = Math.atan2(By,Bx)*180/3.14;
var distB=Math.sqrt(Bx*Bx+By*By);
alert("theta="+theta2+", Dist="+distB);
HolePar[1]=Ax;
HolePar[2]=Ay;
HolePar[3]=Bx;
HolePar[4]=By;
}
//----------------------------------------------------------
```

G2. Moves Stage to Specified Square and Center of Hole

```
//Definition of MoveToHole
function MoveToHole(Salpha, RefInt){    //if there is junk
                                         in the field, it
will affect finding a hole
var i=0;
var Status = "true";
var Int = TakeACCDPictureLow("tohole", "full");
while (Int <= (0.5* RefInt)){
        var TemPosition = MyStage.Position;
        TemPosition.X = TemPosition.X + 0.000006;   //move stage
        6um away
        MyStage.GoTo(TemPosition,3);
        Int = TakeACCDPictureLow("tohole", "full");
        i=i+1;
        if(i>=3) {                       //allow 3
movements
                Status = "false";
                break;
                }
        }
if (Int > (0.5* RefInt)){
        if (Int > (1.1 * RefInt)) Status = "false";  // if square is
                                                       broken
        else {
        var CCDShift = FindDisplacement("tohole", "reftohole");
        // "reftohole" is
reference
//      alert ("hole shift= "+CCDShift.X+", "+CCDShift.Y);
        var Shiftx=CCDShift.X*Math.cos(Salpha) +
        CCDShift.Y*Math.sin(Salpha);
        var Shifty=(-1)*CCDShift.X*Math.sin(Salpha) +
CCDShift. Y*Math.cos(Salpha);
        TemPosition = MyStage.Position;
        TemPosition.X = TemPosition.X - Shiftx;
        TemPosition.Y = TemPosition.Y - Shifty;
        // move stage to hole center
        MyStage.GoTo(TemPosition,3);
        alert ("Check position Ok");
                }
        }
return Status;
}
//----------------------------------------------------------
```

H2. Determines Angle Between CCD Anxis and Stage Axis

```
//Definition of GetStageAlpha
function GetStageAlpha( ){
var TemPosition = MyStage.Position;
TakeACCDPictureLow("Salpha0", "full");
TemPosition.X = TemPosition.X = 0.000002;  //move 2um away
MyStage.GoTo(TemPosition,3);
TakeACCDPictureLow("Salpha1", "full");
```

```
var ShiftDisplacement = FindDisplacement("Salpha1", "Salpha0");
var ratio=ShiftDisplacement.Y/ShiftDisplacement.X;
var angle=Math.atan(ratio);
var angle1=180*angle/3.14;
message="\n Stage alpha angle = "+ angle1+"degree";
DisplayEvent(message);
return angle;
}
//***********************************************************
//----------------------------------------------------------
```

Example 5

Hole Centering Algorithm

A specific example of computer code capable of centering the electron beam in a hole is given below. This specific code is to be utilized with a Tecnai 12 electron microscope using the scripts that are provided therein and the subroutines given in Example 4. Alternatively, subroutines that carry out the same or a similar function that are present in other microscope control systems, or that are created by a user can be utilized.

```
// find the center of the hole
        var CCDShift = FindHoleCenter( );
        var Shiftx=CCDShift.X*Math.cos(alpha) -
        CCDShift.Y*Math.sin(alpha);
        var Shifty=CCDShift.X*Math.sin(alpha) +
        CCDShift.Y*Math.cos(alpha);
                var SearchImgBeamShift = MyProj.ImageBeamShift;
                SearchImgBeamShift.X = InitialImgBeamShift.X -
                Shiftx;
                SearchImgBeamShift.Y = InitialImgBeamShift.Y -
                Shifty;
                var FocusShift2 = MyProj.ImageBeamShift;
                FocusShift2.X = FocusShift.X - Shiftx;
                FocusShift2.Y = FocusShift.Y - Shifty;
                var ExposureShift = MyProj.ImageBeamShift;
                ExposureShift.X = InitialImgBeamShift.X - Shiftx;
                ExposureShift.Y = InitialImgBeamShift.Y - Shifty;
```

Figure 4A:
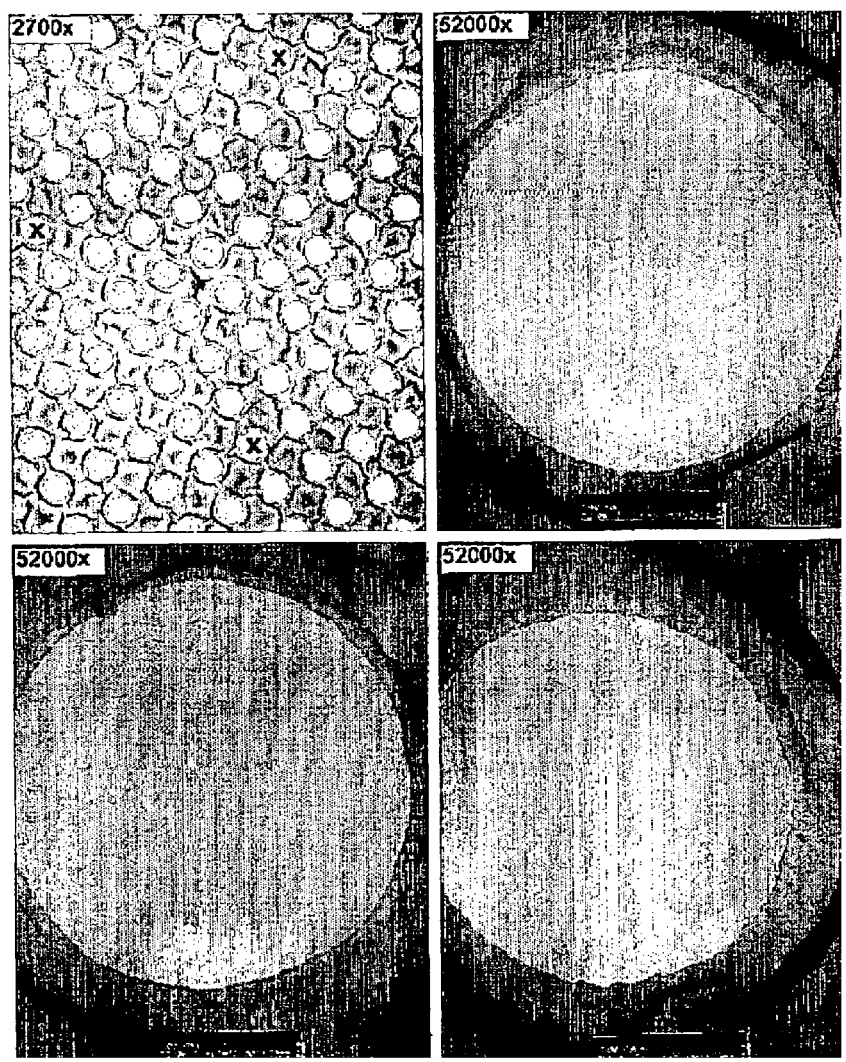
FIG. 4A is a set of electron microscopic image illustrating one aspect of the processes of the invention.

Conditions(SearchMag,SearchInt,SearchDefocus, SearchSpot, SearchImgShift, SearchImgBeamShift);

FIG. 4 illustrates the determination of the accuracy of the automatic hole centering algorithm. FIG. 4A depicts an image of a Quantifoil® grid (R1.2/1.3) at various levels of magnification under conditions necessary to select positions for imaging (indicated by Xs), and the actual images recorded in an automated data collection session. It provides a graphical illustration of the effectiveness of the hole centering algorithm by displaying representative images recorded in a typical automated data collection session. By using the hole centering algorithm, a majority of the hole area is included in the recorded image.

Figure 4B:
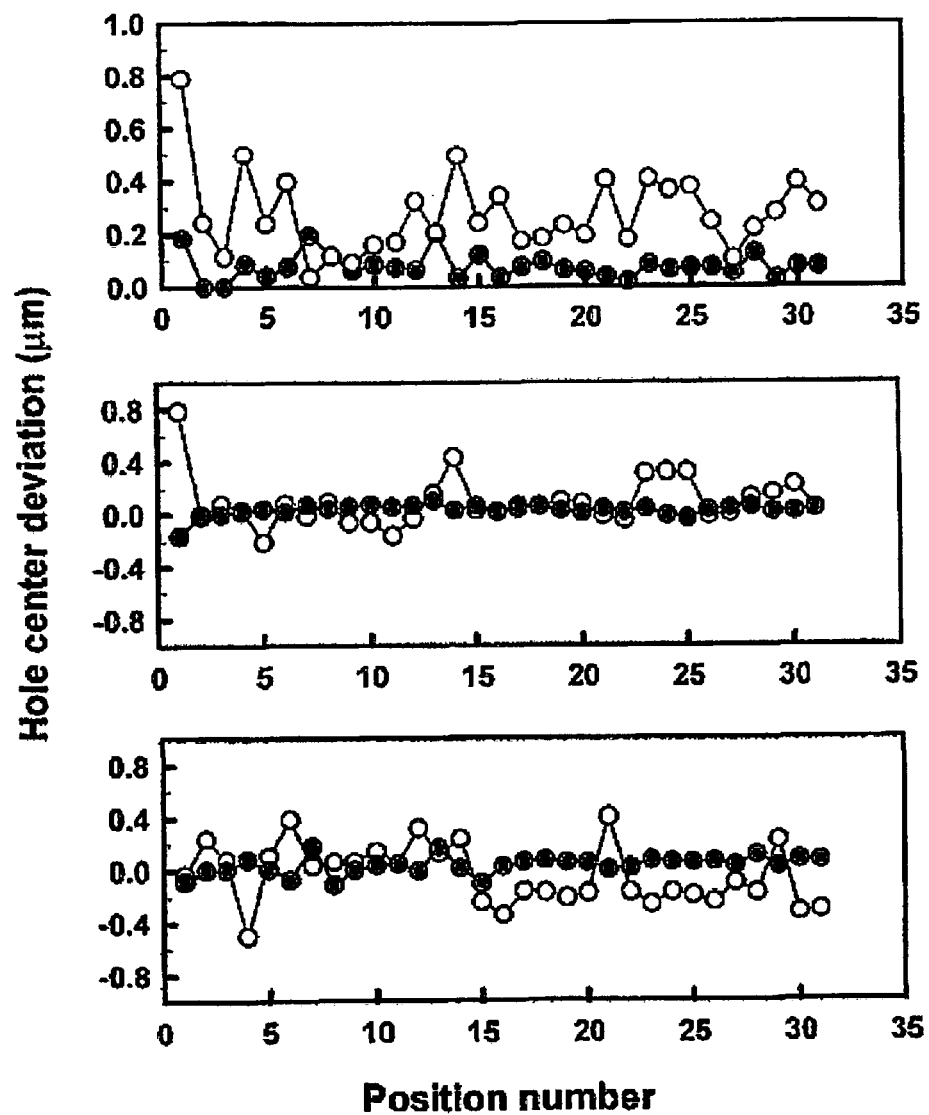
FIG. 4B is a graphical depiction of the results of the study illustrated in FIG. 4a showing Hole Center Deviation versus Position Number.

FIG. 4B shows the quantification of the positional accuracy of centering the hole in the field of view with (closed circle) and without (open circle) use of the automatic hole-centering algorithm. The three panels in FIG. 4B show the extent of the displacement as a net radial value (top), and along two orthogonal directions (middle and bottom).

Without using the hole centering algorithm, the mechanical "wobble" of the goniometer results in hole displacements that can be greater than 0.6 µm even when great care is exercised to manually center holes before they are picked in the Search mode. At 52,000× magnification, this level of uncertainty is generally unacceptable because it can result in the majority of the hole being moved out of the area that is eventually imaged. Analysis of the direction of the displacements reveals that they arise predominantly from errors in positioning along, rather than perpendicular to the long axis of the specimen stage. Use of the hole centering algorithm results in lowering the positional errors to an average displacement of 0.07 μm, which corresponds to the inclusion, on average, of about 90% of the hole in the imaged area.

Example 6
Grid Searching Algorithm

A specific example of computer code to search sections of an electron microscope grid is given below. This specific code is to be utilized on a Tecnai 12 electron microscope using the scripts that are provided therein and the subroutines provided in Example 4. Alternatively, subroutines that carry out the same or a similar function that are present in other microscope control systems, or that are created by a user can be utilized.

```
if (SelectLocationMethod = =2){
autoloop:
var TempSquarePosition = SquareStartPosition;
Gridouterloop:
for(var iii=1;iii<=MaxRowSquare; iii=iii+1){
//goto a direction
Gridinnerloop1:
if (confirm(" Click OK exit Gridscan, Click CANCEL to continue "))
break Gridouterloop;
for (var kkk=1; kkk<=2; kkk=kkk+1){
    for(var jjj=1;jjj<=iii;jjj=jjj+1){
        MyLowDose.BeamBlanked = eOn;
```

-continued

```
        if(kkk= =1){
            TempSquarePosition.X = TempSquarePosition.X + GridPar[1] *
Math.pow(-1,iii+1);
            TempSquarePosition.Y = TempSquarePosition.Y + GridPar[2] *
Math.pow(-1,iii+1);
            }
        if(kkk= =2){
            TempSquarePosition.X = TempSquarePosition.X + GridPar[3] *
Math.pow(-1,iii+1);
            TempSquarePosition.Y = TempSquarePosition.Y + GridPar[4] *
Math.pow(-1,iii+1);
            }
    if((Math.abs(TempSquarePosition.X)>=0.001) ||
(Math.abs(TempSquarePosition.Y)>=0.001)) break Gridouterloop;
    MyStage.GoTo(TempSquarePosition,3);    //move to a square
    TimeDelay(0.5);
```

Example 6
High Level of Automation

A specific example of computer code that could be utilized on a Tecnai 12 electron microscope using the scripts that are provided therein to carry out all three methods of the invention discussed above is given below. This specific code utilizes the scripts provided in the user software and the subroutines given above in Example 4. The code prompts the user for parameters, and depending on the parameters specified, the user inherently chooses a level of automation. Alternatively, subroutines that carry out the same or a similar function that are present in other microscope control systems, or that are created by a user can be utilized.

```
//xxxxxxxxxxxxxxxxxxxxxxxxxxxxxxxxxxxxxxxxxxxxxxxxxxxxxxxxxx
x
//
//Tecnai variables
varMyTecnai = new ActiveXObject("Tecnai.Instrument");
var MyIllum = MyTecnai.Illumination;
varMyProj = MyTecnai.Projection;
varMyCamera = MyTecnai.Camera;
varMyStage = MyTecnai.Stage;
varMyVacuum = MyTecnai.Vacuum;
//TIA variables
varMyTia = new ActiveXObject("ESVision.Application");
varMyAcqMan = MyTia.AcquisitionManager();
varMyCCD = MyTia.CCDServer;
varMyMath = MyTia.ProcessingSystem();
//Low Dose variables
var MyLowDose = new ActiveXObject("LdServer.LdSrv");
//other global variables
var Positions = new Array(); //stores selected positions
var message;       //messages for display in event window
var Err;
var Repeat;
var SetUpFile;
var GridType;
var MaxRowHole ;
var MaxRowSquare =20;
var GridPar = new Array();
var HolePar = new Array();
var Mode;
var LDStatus;
var LDState;
var LDExposeStatus;
var ProgressStatus;
var_result;
var AutoFocusSet = -0.000003; //3um defocus preset for 2nd autofocus
measuring
    var ImageSize;
    var FileDir;
    //var AvgPixInt;
```

-continued

```
    //enumerations
    var eOn = 1;
    var eOff = 0;
    var eYes = 1;
    var eSearch = 0;
    var eFocus1 = 1;
    var eFocus2 = 2;
    var eExposure = 3;
    var eReady = 1;
    var eStart = "true";
    var eAbort = "false";
    var eInExpose = 1;
    //----------------------------------------------------------
    //***********************************************************
    //                    Main function starts here
    //***********************************************************
    //
    //******************start initialization*******************
    function OnAutomation(){
    message="\n Start running automation";
    DisplayEvent(message);
    ProgressStatus = "true";
    //variables retrieved from form
    var SearchMag = document.MainForm.SearchMag.selectedIndex; //0–38
    //var SearchDefocus = document.MainForm.SearchDefocus.value; //in
microns
    var SearchDefocus = −20;
    var SearchSpot = document.MainForm.SearchSpotSize.selectedIndex; //0–10
    var ExposureMag = document.MainForm.ExposureMag.selectedIndex; //0–38
    var ExposureDefocus = document.MainForm.ExposureDefocus.value; //in
micorns
    var ExposureDefocusStep =
document.MainForm.ExposureDefocusStep.value;
    var PictInterval = document.MainForm.Interval.value;
    var ExposureSpot = document.MainForm.ExposureSpotSize.selectedIndex;
//0–10
    var FocusMag = document.MainForm.FocusMag.selectedIndex; //0–38
    //var FocusDefocus = document.MainForm.FocusDefocus.value; //in microns
    var FocusDefocus = 0;
    var FocusSpot = document.MainForm.FocusSpotSize.selectedIndex; //0–10
    vra DriftRate = document.MainForm.Drift.value; //entered in angstroms
    var FilmorCCD = document.MainForm.FilmorCCD.selectedIndex; //Film=0,
CCD=1
    var IceMax = document.MainForm.IceThickMax.value;
    var IceMin = document.MainForm.IceThickMin.value;
    var SelectLocationMethod =
document.MainForm.select_method.selectedIndex; //manual=0, semi-auto=1, auto=2
    if(SelectLocationMethod ==2){
        for ( var k=1; k<=5; k++){ //alow max 5 repeat calibrations
            GetGridPar();
            if(confirm("Finish grid calibration? \n Click Ok continue, Click
Cancel to repeat "))
            break;
        }
        alert("Place the stage to center of square, at center of the grid");
        var SquareStartPosition = MyStage.Position;
        alert("Go back to search mag, Find a target");
        }
    else if (SelectLocationMethod ==1 ){
        alert ("store locations of good squares!");
        var CaptureType =3;
        var SquaresNumber = StoreLocations(CaptureType);
        alert("Go back to search mag, FInd a target");
        }
    FileDir = document.MainForm.FileDir.value;
    GridType = document.MainForm.GridType.selectedIndex;
    if (Grid Type ==0) MaxRowHole = 20;
    else if (GridType ==1) MaxRowHole = 17;
    else if (GridType ==2) MaxRowHole = 13;
    else if (GridTYpe ==3) MaxRowHole = 8;
    else MaxRowHole = 5;
    if (GridType ==0 ||GridType==1) {
        SetUpFile="searchhole12";
        ImageSize = 128;
    }
    else{
        SetUpFile="searchhole24";
        ImageSize = 256;
    }
```

-continued

```
    //modifying variables to conform to program
    SearchMag = SearchMag + 1; //+1 difference from html to Tecnai, 0 for
diffraction mode
    SearchDefocus = SearchDefocus/1000000; //microns to meters
    ExposureMag = ExposureMag + 1; //+1 difference from html to Tecnai
    ExposureDefocus = ExposureDefocus/1000000; //microns to meters
    ExposureDefocusStep = ExposureDefocusStep/1000000; //microns to meters
    FocusMag = FocusMag + 1; //+1 difference from html to Tecnai
    //FocusDefocus = FocusDefocus/1000000; //microns to meters
    SearchSpot = SearchSpot + 1; //+1 diference from html to Tecnai, 1–11
spotsize in Tecnai
    FocusSpot = FocusSpot + 1;
    ExposureSpot = ExposureSpot + 1;
    var ExpNumStat=MyCamera.ExposureNumber; // get film start number
    //Insert CCD camera
    try {
        MyCCD.CameraInserted = true;
        }
    catch (err){
        DisplayError(Err);
    }
    //activate low dose fucntion
    if (MyLowDose.LowDoseAvailable != eYes){
    message = "\nLow Dose is not available, Stop automation!";
    DisplayEvent(message);
    }
    ActiveLowDose();
    //ensure that the beam is blanked
    MyLowDose.BeamBlanked = eOn;
    //Setup LD conditions
    //go to LD Search mode, get the search/exposure shift
    SearchMode();
    var SearchShiftX = MyProj.ImageShift.X;
    var SearchShiftY = MyProj.ImageShift.Y;
    //go to LD Focus mode, get the Focus shift distance
    FocusMode();
    varFocusShiftX = MyProj.ImageBeamShift.X;
    varFocusShiftY = MyProj.ImageBeamShift.Y;
    //go to LD exposure mode, this LD mode is used for all purpose
    ExposureMode();
    //set search shift and focus shift
    var InitialImgShift = MyProj.ImgaeShift;
    var InitialImgBeamShift = MyProj.ImageBeamShift;
    var SearchImgShift = MgProj.ImageShift;
    SearchImgShift.X = SearchShiftX;
    SearchImgShift.Y = SearchShiftY;
    var FocusShift = MyProj.ImageBeamShift;
    FocusShift.X = FocusShiftX;
    FocusShift.Y = FocusShiftY;
    //define intensity for search mode
    //ensure that the beam is blanked
    //MyLowDose.BeamBlanked = eOn;
    var SearchInt = MyIllum.Intensity;
    SearchInt = 0.50; //0.50 should produce a visible beam
    //go to search mode
    Conditions(SearchMag,SearchInt,SearchDefocus,SearchSpot, SearchImgShift,
InitialImgBeamShift);
    //if the target is not at point (alignment is not good), start over again.
    MyLowDose.BeamBlanked = eOff;
    alert ("check if the target is at pointer.");
        if (confirm("Misaligned, to RESET? \n Click OK to reset, Click
CANCEL to continue ")){
        OnReset();
        ProgressStatus = "false";
        }
    //ensure that the beam is unblanked
    MyLowDose.BeamBlanked = eOff;
    if (SelectLocationMethod ==0 ){        //manual mode
        //store locations of interest
        var LocationsNumber = StoreLocations(FilmorCCD); //FilmorCCD
will indicate the maximum number of locations
        }
    else if (SelectLocationMethod ==1 ||SelectLocationMethod ==2){
                        //auto or semi-auto mode
        for ( var k=1; k<=5; k++){ //alow max 5 repeat calibrations
        GetHolePar();
        if (confirm(" Finish hole calibration? \n Click OK continue, Click
CANCEL to repeat "))
        break;
```

```
            }
        }
    alert("Click OK to enter the correct beam width settings for search mode");
    //stores beam width settings
    SearchInt = MyIllum.Intensity;
    //Preparing a hole reference image
    alert("Please move the stage to a HOLE CENTER where you DO NOT want
to take a picture.\n PLEASE MOVE TO AN HOLE CENTER. \n PUT DOWN THE
SMALL SCREEN AND REMOVE THE POINTER!!! ");
    //Get alpha
    var alpha=GetAlpha();
    //Prepare reference hole for hole centering
    var SumRefInt = TakeACCDPictureLow("refhole", "small");
    // Find avgerage intensity of an empty hole for ice thickness determination
    TakeACCDPictureLow("emptyhole", "small");
    var AvgIntHole = GetAvgPixInt("emptyhole");
    //prepare a full size reference for semiaoto and auto hole sprial scan
    var SumRefIntFull = TakeACCDPictureLow("reftohole", "full");
    var StageAlpha = GetStageAlpha();
    //define initial conditions for exposure mode
    MyCamera.MainScreen = 3;          //puts the main screen down
    var ExpInt = MyIllum.Intensity;
    var BurnIceInt = MyIllum.Intensity;
    ExpInt = 0.45; //0.45 should produce a visible beam.
    //go to exposure mode
    Conditions(ExposureMag,ExpInt,0,ExposureSpot,
InitialImgShift,InitialImgBeamShift );
    //ensure that the beam is unblanked
    MyLowDose.BeamBlanked = eOff;
    alert("Click OK to enter the correct beam width settings for exposure mode. \n
FOCUS AND RESET DEFOCUS.\n PUT DOWN THE SMALL SCREEN AND
REMOVE THE POINTER.");
    //stores beam width settings
    ExpInt = MyIllum.Intensity;
    ExposureSpot = MyIllum.SpotSizeIndex;
    ExposureMag = MyProj.MagnificationIndex;
    alert("Click OK to enter the correct beam width settings for burn ice in the
hole");
    BurnIceInt = MyIllum.Intensity;
    //Stops acquiring if TIA was left on
    var State = MyTia.AcquisitionManager().IsAcquiring();
    if (State == true){
       MyAcqMan.Stop();
    }
    //centers the beam and stores the location as the exposure mode center
    BeamCenter();
    var PreviousExpCenter = MyIllum.Shift;
    //define initial conditions for focus mode
    var FocusInt = MyIllum.Intensity;
    FocusInt = 0.43;
    //go to focus mode
    Conditions(FocusMag,FocusInt,FocusDefocus,FocusSpot, IntialImgShift,
FocusShift);
    //ensure that the beam is unblanked
    MyLowDose.BeamBlanked = eOff;
    alert("Click OK to enter the correct beam width settings for focus mode.");
    //stores beam width settings
    FocusInt = MyIllum.Intensity;
    FocusSpot = MyIllum.SpotSizeIndex;
    FocusMag = MyProj.MagnificationIndex;
    //Stops acquiring if TIA was left on
    State = MyTia.AcquisitinManager().IsAcquiring();
    if (State == true){
       MyAcqMan.Stop();
    }
    //centers the beam and stores the location as the focus mode center
    BeamCenter();
    varPreviousFocusCenter = MyIllum.Shift;
    //leave to search condition nad blank beam for following procedures
    MyLowDose.BeamBlanked = eOn;
    Conditions(SearchMag,SearchInt,SearchDefocus,SearchSpot, SearchImgShift,
InitialImgBeamShift);
    if (confirm("Satisfied with initialization? \n Click OK to RESET, Click
CANCEL to continue ")){
         OnReset();
         ProgressStatus = "false";
         }
    //*********Three different modes of the method start here **************
    if (ProgressStatus == "true"){
```

```
    alert ("Now you are ready to collect data");
    var ImageNum = 0;
    var HoleNum = 0;
//-----------this loop is for manual selection--------------------------
    if (SelectLocationMethod ==0){
//loop for move to location, auto hole centering, drift, focus, picture taking
    manualloop:
    for (var i=1;i<=LocationsNumber,i=i+1){
    alert(i);
//if (confirm(" Click OK exit, Click CANCEL to continue "))
//break manualloop;
//ensure that the beam is blanked
    MyLowDose.BeamBlanked = eOn;
        //go to position
        GoToLocation(i);
        TimeDelay(0.5);   // finish the action before switch mode
    // Go to Search mode
        Conditions(SearchMag,SearchInt,SearchDefocus,SearchSpot,
SearchImgShift, InitalImgBeamShift);
        Mode="search";
    // find the center of the hole
        var CCDShift = FindHoleCenter();
        var Shiftx=CCDShift.X*Math.cos(alpha) - CCDShift.Y*Math.sin(alpha);
        var Shifty=CCDShift.X*Math.sin(alpha) + CCDShift.Y*Math.cos(alpha);
            var SearchImgBeamShift = MyProj.ImageBeamShift;
            SearchImgBeamShift.X = InitialImgBeamShift.X - Shiftx;
            SearchImgBeamShift.Y = InitialImgBeamShift.Y - Shifty;
            var FocusShift2 = MyProj.ImageBeamShift;
            FocusShift2.X = FocusShift.X - Shiftx;
            FocusShift2.Y = FocusShift.Y - Shifty;
            var ExposureShift = MyProj.ImageBeamShift;
            ExposureShift.X = InitialImgBeamShift.X - Shiftx;
            ExposureShift.Y = InitialImgBeamShift.Y - Shifty;
        Conditions(SearchMag,SearchInt,SearchDefocus,SearchSpot,SearchImgShift,
SearchImgBeamShift);
        TakeACCDPictureLow("icehole", "small"); // Take a low mag ccd image in
search mode
        alert("check if holecentered");
            var AvgIntIce = GetAvgPixInt("icehole");
        //skip the location if ice is not ok
            var IceThickness = 7500 * (-1) * Math.LOG10E *
Math.log(Math.LOG10E*Math.log(10*AvgIntIce/AvgIntHole));
        alert("ice thickness="+IceThickness);
        message="\n Ice thickness=" + IceThickness;
        DisplayEvent(message);
        if ((IceThickness <= IceMax) && (IceThickness >= IceMin ))
        {
        //go to focus mode
            Conditions(FocusMag,FocusInt,FocusDefocus,FocusSpot, InitialImgShift,
FocusShift2);
        MyCamera.MainScreen = 3;         //puts the main screen down
            Mode="focus";
        //ensure that the beam is unblanked
            MyLowDose.BeamBlanked = eOff;
        //center the beam
            MyIllum.Shift = PreviousFocusCenter; //bring the beam roughly on screen
        TimeDelay(0.5); //get beam settled before BeamCenter()
            BeamCenter();
            PreviousFocusCenter = MyIllum.Shift; //store focus beam center
        //expose for 10 seconds to burn ice without lifting screen
            CCDExpose(8);
        //Find Drift
            var driftstatus = FindDrift(DriftRate);
        //alert("driftstatus="+driftstatus);
        //set focus
            if ( i % PicInterval ==0) {
            ExposureDefocus=ExposureDefocus+ ExposureDefocusStep;
            }     //Increase expsore defocus bby step every # of pictures
        message="\n Defocus = " + ExposureDefocus;
        DisplayEvent(message);
            AutoFocus();
            var focustatus = AutoFocus2();
        //ensure that the beam is blanked
        MyLowDose.BeamBlanked = eOn;
        //skip the location if drifting or focusing problem occures
            if((driftstatus == "true") && (focusatus == "true")){
        //go to exposure mode
            Conditions(ExposureMag, ExpInt, ExposureDefocus,ExposureSpot,
InitialImgShift, ExposureShift);
```

```
        Mode="exposure";
    //shift beam to previous centered position
        MyIllum.Shift = PreviousExpCenter;
        ImageNum = ImageNum+1;
    //take a picture
        if (FilmorCCD == 0){
    message="\n Taking a film picture #" + MyCamera.ExposureNumber
+"("+ImageNum+")";
    DisplayEvent(message);
            TakeALDFilmPicture();
        }
        else{
            TakeACCDPicture(i);
    message="\n Taking a CCD picture # "+ ImageNum;
    DisplayEvent(message);
        }
    }                   //end if focus and drift ok
    }                   //end if ice ok
    //do beam center and emptyhole Int measureing every 4 pictures
            if ( i % 4 ==0) {
        Conditions(ExposreMag, ExpInt, ExposureDefocus,ExposureSpot,
InitialImgShift, ExposureShift);
        Mode="exposure";
    //ensure that the beam is unblanked
        MyLowDose.BeamBlanked = eOff;
        TimeDelay(0.25);
    //center the beam
        BeamCenter();
    //store the beamshift center for exposure mode
        PreviousExpCenter = MyIllum.Shift;
    //renew the avg pix int from a empty hole
        BurnAHole(BurnIceInt);
    // Go to Search mode
        Conditions(SearchMag,SearchInt.SearchDefocus,SearchSpot,
SearchImgShift, SearchImgBeamShift); //bring hole to the center using
imgBeamShift
    // MyLowDose.BeamBlanked = eOff;
        TakeACCDPictureLow("emptyhole", "small");
        AvgIntHole = GetAvgPixInt("emptyhole");
            }   //measure empty hole beam int every 4 picture as reference for
ice
        MyLowDose.BeamBlanked = eOn;
        Conditions(SearchMag,SearchInt,SearchDefocus,SearchSpot,
SearchImgShift, InitialImgBeamShift);
        }                   //end location loop
        HoleNum = i-1;
    }                   //end if mode =manual
    //------------------manual selection loop finishes here--------------------
    //------------------semiauto mode starts here------------------------------
    if (SelectLocationMethod ==1){
    semiautoloop:
    for (var i=1;i<=SquaresNumber;i=i+1){              //location loop
    //if (confirm("continue aemiauto loop \n Click OK exit, Click CANCEL to
continue "))
    //break semiautoloop;
        MyLowDose.BeamBlanked = eOn;
            //go to position
            GoToLocation(i);
        TimeDelay(0.5);   // finish the action before switch mode
    // Go to Search mode
        Conditions(SearchMag,SearchInt,SearchDefocus,SearchSpot,
SearchImgSHift, InitialImgBeamShift);
    //move stage to center of a hole
        var squarestatus = MoveToHole(StageAlpha, SumRefIntFull);
        if (squarestatus == "true"){            //do hole scan in a
square if square is good
    //start spiral scan of holes
        var TempPosition = MyStage.Position;
        outerloop:
        for(var ii=1,ii<=MaxRowHole; ii=ii+1){
    //goto a direction
        innerloop1:
        if(confirm(" crosscor # "+ii+"\n Click OK exit, Click CANCEL to continue
"))
        break outerloop;
        for (var kk=1; kk<=2;kk=kk+1){
            var BadCount = 0;
            for(var jj=1;jj<=ii; jj=jj+1){
                if (kk==1){
```

-continued

```
            TempPosition.X = TempPosition.X + HolePar[1] * Math.pow(-
1,ii+1);
            TempPosition.Y = TempPosition.Y + HolePar[2] * Math.pow(-
1,ii+1);
            }
            if (kk==2){
            TempPosition.X = TempPosition.X + HolePar[3] * Math.pow(-
1,ii+1);
            TempPosition.Y = TempPosition.Y + HolePar[4] * Math.pow(-
1,ii+1);
            }
        if ((Math.abs(TempPosition.X)>=0.001) ||
(Math.abs(TempPosition.Y)>=0.001)) break outerloop;
        MyStage.GoTo(TempPosition,3);
        TimeDela(0.5);
        HoleNum = HoleNum+1;
    var SumInt = TakeACCDPictureLow("hole", "small");
    if (SumInt<=(0.5*SumRefInt)) BadCount = BadCount +1;
    if (BadCount >=2) break outerloop;        //if two continue holes black, exit
hole scan
    //---------------start collect image-------------
    if (SumInt > (0.5 * SumRefInt)){
    // find the center of the hole
        var CCDShift = FIndHoleCenter();
        var Shiftx=CCDShift.X*Math.cos(alpha) - CCDShift.Y*Math.sin(alpha);
        var Shifty=CCDShift.X*Math.sin(alpha) + CCDShift.Y*Math.cos(alpha);
            var SearchImgBeamShift = MyProj.ImageBeamShift;
            SearchImgBeamShift.X = InitialImgBeamShift.X - Shiftx;
            SearchImgBeamShift.Y = InitialImgBeamShift.Y - Shifty;
            var FocusShift2 = MyProj.ImageBeamShift;
            FocusShift2.X = FocusShift.X - Shiftx;
            FocusShift2.Y = FocusShift.Y - Shifty;
            var ExposureShift = MyProj.ImageBeamShift;
            ExposureShift.X = InitialImgBeamShift.X - Shiftx;
            ExposureShift.Y = InitialImgBeamShift.Y - Shifty;
        Conditions(SearchMag,SearchInt,SearchDefocus,SearchSpot, SearchImgShift,
SearchImgBeamShift);
        TakACCDPictureLow("icehole", "small"); // Take a low mag ccd image in
search mode
        alert("check holecentered");
            var AvgIntIce = GetAvgPixInt("icehole");
        //skip the location if ice is not ok
            var IceThickness = 7500 * (-1) * Math.LOG10E *
Math.log(Math.LOG10E*Math.log(10*AvgIntIce/AvgIntHole));
            alert("ice thickness="+IceThickness);
            message="\n Ice thickness=" + IceThickness;
            DisplayEvent(message);
            if ((IceThickness <= IceMax) && (IceThickness >= IceMin))
            {
            //go to focus mode
            Conditions(FocusMag,FocusInt,FocusDefocus,FocusSpot, InitialImgShift,
FocusShift2);
        MyCamera.MainScreen = 3;            //puts the main screen down
            Mode="focus";
        //ensure that the beam is unblanked
            MyLowDose.BeamBlanked = eOff;
        //center the beam
            MyIllum.Shift = PreviousFocusCenter; //bring the beam roughly on screen
            TimeDelay(0.5); //get beam settled before BeamCenter()
            BeamCenter();
            PreviousFocusCenter = MyIllum.Shift; //store focus beam center
        //expose for 10 seconds to burn ice without lifting screen
            CCDExpose(8);
        //Find Drift
            var drifstatus = FindDrift(DriftRate);
        //set focus
            if ( ImageNum % PicInterval ==0) {
            ExposureDefocus=ExposureDefocus+ ExposureDefocusStep;
            }      //Increase exposure defocus bby step every # of pictures
        message="\n Defocus = " + ExposureDefocus;
        DisplayEvent(message);
            AutoFocus();
            var focustatus = AutoFocus2();
        //ensure that the beam is blanked
        MyLowDose.BeamBlanked = eOn;
        //skip the location if drifting or focusing problem occures
            if ((driftstatus == "true") && (focustatus == "ture")){
        //go to exposure mode
            Conditions(ExposureMag, ExpInt. ExposureDefocus,ExposureSpot,
```

-continued

```
InitialImgShift, ExposureShift);
      Mode="exposure";
    //shift beam to previous centered position
      MyIllum.Shift = PreviousExpCenter;
      ImageNum = ImageNum+1;
    //take a picture
      if (FilmorCCD == 0){
    message="\n Taking a film picture #" + My Camera.ExposureNumber
+"("+ImageNum+")";
    DisplayEvent(message);
        TakeALDFilmPicture();
      }
      else{
        TakeACCDPicture(ImageNum);
    message="\n Taking a CCD picture # "+ ImageNum;
    DisplayEvent(message);
      }
      }         //end if dfrift and focus
      }         // end of ice thick ok
      }         //end of SumInt>0.5*SumRefInt, for hole with no
contamination
    //do beam center and emptyhole Int measureing every 4 pictures
        if ( HoleNum % 4 ==0) {
        Conditions(ExposureMag, ExpInt, ExposureDefocus,ExposureSpot,
InitialImgShift, ExposureShift);
      Mode="exposure";
    //ensure that the beam is unblanked
      MyLowDose.BeamBlanked = eOff;
      TimeDelay(0.25);
    //center the beam
      BeamCenter();
    //store the beamshift center for exposure mode
      PreviousExpCenter = MyIllum.Shift;
    //renew the avg pix int from a empty hole
      BurnAHole(BurnIceInt);
      // Go to Search mode
      Conditions(SearchMag,SearchInt,SearchDefocus,SearchSpot,
SearchImgShift, SearchImgBeamShift); //bring hole to the center using
imgBeamShift
      // MyLowDose.BeamBlanked = eOff;
      SumRefInt = TakeACCDPictureLow("emptyhole", "small");
      AvgIntHole = GetAvgPixInt("emptyhole");
        }    //measure empty hole beam int every 4 picture as reference for
ice
      MyLowDose.BeamBlanked = eOn;
      Conditions(SearchMag,SearchInt,SearchDefocus,SearchSpot,
SearchImgShift, InitialImgBeamShift);
      //--------------------end image collection-----------------
      }          //end innerloop1
      }          // end of kk loop for both directions
      }              //end outerloop
      }              //end of if squarestatus
      // SumRefIntFull = TakACCDPictureLow("emptyholefull", "full");
      }              //end location loop
      }
      //------------------semiauto loop finishes here------------------------
      //------------------auto loop starts here ---------------------------
      if (SelectLocationMethod ==2){
      autoloop:
      var TempSquarePosition = SquareStartPosition;
      Gridouterloop:
      for(var iii=1;iii<=MaxRowSquare; iii=iii+1){
      //goto a direction
      Gridinnerloop1:
      if (confirm(" Click OK exit Gridscan, Click CANCEL to continue "))
      break Gridouterloop;
      for (var kkk=1; kkk<=2; kkk=kkk+1){
          for(var jjj=1;jjj<=iii; jjj=jjj+1){
              MyLowDose.BeamBlanked = eOn;
              if (kkk==1){
              TempSquarePosition.X = TempSquarePosition.X + GridPar[1]
* Math.pow(-1,iii+1);
              TempSquarePosition.Y = TempSquarePosition.Y + GridPar[2]
* Math.pow(-1,iii+1);
              }
              if (kkk==2){
              TempSquarePosition.X = TempSquarePosition.X + GridPar[3]
* Math.pow(-1,iii+1);
              TempSquarePosition.Y = TempSquarePosition.Y + GridPar[4]
```

-continued

```
* Math.pow(-1,iii+1);
        }
        if ((Math.abs(TempSquarePosition.X)>=0.001) ||
(Math.abs(TempSquarePosition.Y)>=0.001)) break Gridouterloop;
        MyStage.GoTo(TempSquarePosition,3);    //move to a square
        TimeDelay(0.5);
    //-----------------following procedures similar to semiauto mode---------------
    // Go to Search mode
        Conditions(SearchMag,SearchInt,SearchDefocus,SearchSpot,
SearchImgShift, InitialImgBeamShift);
        //move stage to center of a hole
        var squarestatus = MoveToHole(StageAlpha, SumRefIntFull);
        if (squarestatus == "true"){                    //do hole scan in a
square if square is good
        //start spiral scan of holes
        var TempPosition = MyStage.Position;
        outerloop:
        for(var ii=1;ii<=MaxRowHole; ii=ii+1){
        //goto a direction
        innerloop1:
        if (confirm(" Click OK exit Holescan, Click CANCEL to continue "))
        break outerloop;
        for (var kk=1; kk<=2;kk=kk+1){
            var BadCount = 0;
            for (var jj=1;jj<=ii; jj=jj+1){
                if (kk==1){
                TempPosition.X = TempPosition.X + HolePar[1] * Math.pow(-
1,ii+1);
                TempPosition.Y = TempPosition.Y + HolePar[2] * Math.pow(-
1,ii+1);
                }
                if (kk==2){
                TempPosition.X = TempPosition.X + HolePar[3] * Math.pow(-
1,ii+1);
                TempPosition.Y = TempPosition.Y + HolePar[4] * Math.pow(-
1,ii+1);
                }
            if ((Math.abs(TempPosition.X)>=0.001) ||
(Math.abs(TempPosition.Y)>=0.001)) break outerloop;
        MyStage.GoTo(TempPosition,3);                // move to a hole
        TimeDelay(0.5);
        HoleNum = HoleNum+1;
    var SumInt = TakeACCDPictureLow("hole", "small");
    if (SumInt<=(0.5*SumRefInt)) BadCount = BadCount +1;
    if (BadCount >=2) break outerloop;      //if two continue holes black, exit
hole scan
    //--------------start collect image-------------
    if (SumInt > (0.5 * SumRefInt)){
    // find the center of the hole
        var CCDShift = FindHoleCenter();
        var Shiftx=CCDShift.X*Math.cos(alpha) - CCDShift.Y*Math.sin(alpha);
        var Shifty=CCDShift.X*Math.sin(alpha) + CCDShift.Y*Math.cos(alpha);
            var SearchImgBeamShift = MyProj.ImageBeamShift;
            SearchImgBeamShift.X = InitialImgBeamShift.X - Shiftx;
            SearchImgBeamShift.Y = InitialImgBeamShift.Y - Shifty;
            var FocusShift2 = MyProj.ImageBeamShift;
            FocusShift2.X = FocusShift.X - Shiftx;
            FocusShift2.Y = FocusShift.Y - Shifty;
            var ExposureShift = MyProj.ImageBeamShift;
            ExposureShift.X = InitialImgBeamShift.X - Shiftx;
            ExposureShift.Y = InitialImgBeamShift.Y - Shifty;
    Conditions(SearchMag,SearchInt,SearchDefocus,SearchSpot, SearchImgShift,
SearchImgBeamShift);
        //alert ("search shifts="+SearchImgShift.X+",
"+SearchImgShift.Y+"\n"+SearchImgBeamShift.X);
        TakeACCDPictureLow("icehole", "small"); // Take a low mag cd image in
search mode
        alert("chech holecentered");
            var AvgIntIce = GetAvgPixInt("icehole");
        //skip the location if ice is not ok
            var IceThickness = 7500 * (-1) * Math.LOG10E *
Math.log(Math.LOG10E*Math.log(10*AvgIntIce/AvgIntHole));
        alert("ice thickness="+IceThickness);
        message="\n Ice thickness=" + IceThickness;
        DisplayEvent(message);
        if ((IceThickness <= IceMax) && (IceThickness >= IceMin ))
        {
        //go to focus mode
            Conditions(FocusMag,FocusInt,FocusDefocus,FocusSpot, InitialImgShift,
```

-continued

```
FocusShift2);
    MyCamera.MainScreen = 3;      //puts the main screen down
       Mode="focus";
    //ensure that the beam is unblanked
       MyLowDose.BeamBlanked = eOff;
    //center the beam
       MyIllum.Shift = PreviousFocusCenter; //bring the beam roughly on screen
       TimeDelay(0.5); //get beam settled before BeamCenter()
       BeamCenter();
       PreviousFocusCenter = MyIllum.Shift; //store focus beam center
    //expose for 10 seconds to burn ice without lifting screen
       CCDExpose(8);
    //Find Drift
       var driftstatus = FindDrift(DriftRate);
    //set focus
       if ( ImageNum % PictInterval ==0) {
          ExposureDefocus=ExposureDefocus+ ExposureDefocusStep;
          }      //Increase exposure defocus bby step every # of pictures
    message="\n Defocus = " + ExposureDefocus;
    DisplayEvent(message);
       AutoFocus();
       var focustatus = AutoFocus2();
    //ensure that the beam is blanked
    MyLowDose.BeamBlanked = eOn;
    //skip the location if drifting or focusing problem occures
       if ((driftsatus == "true") && (focustatus == "true")){
    //go to exposure mode
       Conditions(ExposureMag, ExpInt, ExposureDefocus,ExposureSpot,
InitialImgShift, ExposureShift);
       Mode="exposure";
    //shift beam to previous centered position
       MyIllum.Shift = PreviousExpCenter;
       ImageNum = ImageNum+1;
    //take a picture
       if (FilmorCCD == 0){
    message="\n Taking a film picture #" + MyCamera.ExposureNumber
+"("+ImageNum+")";
       DisplayEvent(message);
          TakeALDFilmPicture();
          }
       else{
          TakeACCDPicture(ImageNum);
       message="\n Taking a CCD picture # "+ ImageNum;
       DisplayEvent(message);
          }
       }        //end if dfrift and focus
       }        // end of ice thick ok
       }        //end of SumInt>0.5*SumRefInt
    //do beam center and emptyhole Int measureing every 4 pictures
       if ( HoleNum % 4 ==0) {
       Conditions(ExposureMag, ExpInt, ExposureDefocus,ExposureSpot,
InitialImgShift, ExposureShift);
       Mode="exposure";
    //ensure that the beam is unblanked
       MyLowDose.BeamBlanked = eOff;
       TimeDelay(0.25);
    //center the beam
       BeamCenter();
    //store the beamshift center for exposure mode
       PreviousExpCenter = MyIllum.Shift;
    //renew the avg pix int from a empty hole
       BurnAHole(BurnIceInt);
       // Go to Search mode
       Conditions(SearchMag,SearchInt,SearchDefocus,SearchSpot,
SearchImgShift, SearchImgBeamShift); //bring hole to the center using
imgBeamShift
    // MyLowDose.BeamBlanked = eOff;
       SumRefInt = TakeACCDPictureLow("emptyhole", "small");
    // SumRefIntFull = TakeACCDPictureLow("emptyholefull", "full");
       AvgIntHole = GetAvgPixInt("emptyhole");
       }    //measure empty hole beam int every 4 picture as reference for
ice
       MyLowDose.BeamBlanked = eOn;
       Conditions(SearchMag,SearchInt,SearchDefocus,SearchSpot,
SearchImgShift, InitialImgBeamShift);
    //---------------------end image collection----------------
       }              //end innerloop1
       }              // end of kk loop for both directions
       }                   //end outerloop
```

-continued

```
}                       //end of it squarestatus
//--------------finish procedures similar to semiauto mode-------
        }               //end Gridinner loop1
    }                   //end of kkk loop for both direction
    }                   //end Gridouter loop
}
//-----------------auto loop finishes here----------------------
}                       //end if ProgressStatus
//***********resetting microscope and log film number************
//return microscope to search mode
SearchMode();
//ensure that the beam is unblanked
MyLowDose.BeamBlanked = eOff;
   Mode="search";
//put the main screen down
MyCamera.MainScreen = 3;
MyCCD.CameraInserted = false;      // retract CCD camera
alert("Done");
//log the exposure numbers
    message="\nTotal hole number="+HoleNum+"\nTotal image
number="+ImageNum;
    DisplayEvent(message);
        if (FilmorCCD == 0){
    var ExpNumEnd=MyCamera.ExposureNumber-1;
    var FilmNumber="\n Exposure Number:" + ExpNumStart +"---" +
ExpNumEnd;
        DisplayEvent(FilmNumber);
    document.MainForm.ExpNum.value=ExpNumStart+"---" + ExpNumEnd;
    }
    message="\n DONE!!!";
    DisplayEvent(message);
}
//-----------------------------------------------------------
```

Figure 5A:
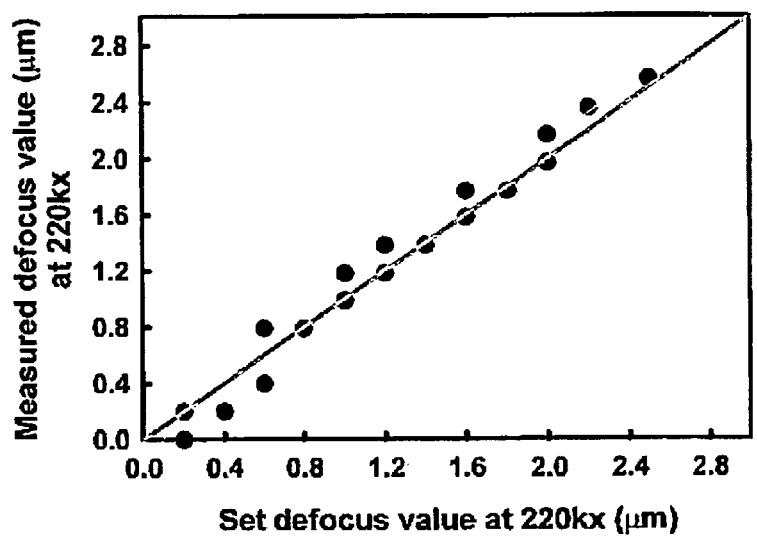
FIGS. 5A and 5B are a graphical depictions of the Measured Defocus Value at 220 kx using one embodiment of the invention.
Figure 5B:
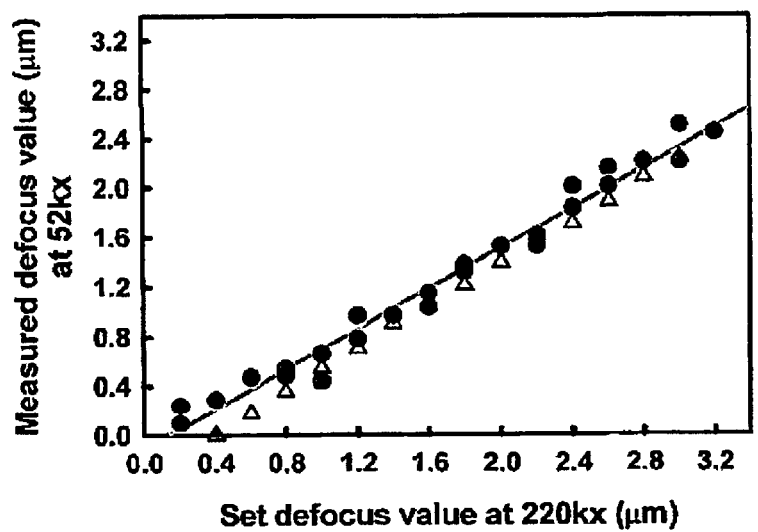

FIG. 5 illustrates different aspects of the accuracy of the automated focus determination procedure. FIG. 5A shows the intrinsic accuracy of the algorithm that we employed to calculate the deviation from focus by plotting the value returned by the program vs. the value manually set at the same magnification (220,000×). The slope of this plot is close to 1, establishing the reliability of the focus determination procedure. In a normal low-dose imaging session, however, the focus is set at a higher magnification, while the image is recorded at a lower magnification. The extent of the change in focus between the different magnifications is different for each microscope, and can sometimes be significant. The As in FIG. 5B shows the extent of this difference determined manually, over a range of underfocus values for typical Focus and Exposure magnification settings used in our laboratory. Here, the measured values come from determination of Thon ring spacing in images recorded on film at 52,000×. Since the automated procedure should essentially mimic the manual low-dose operation, the experimentally measured underfocus values at 52,000× should bear the same relation to the filled symbols (●) in the calibration curve in FIG. 5B.

Figure 6:
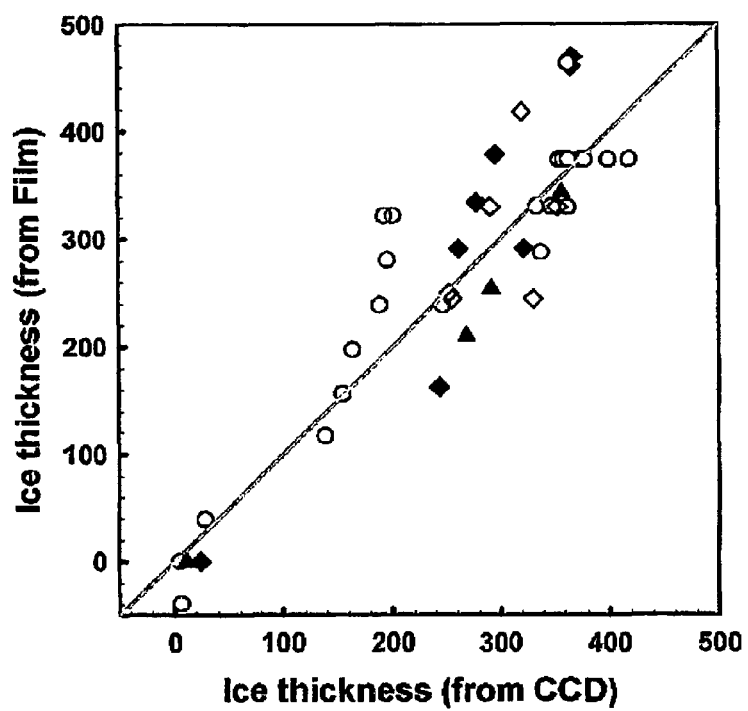
FIG. 6 is a graphical depiction of an assessment of ice thickness at low magnification versus ice thickness at high magnification.

FIG. 6 shows the effectiveness of the method in assessing the thickness of the vitreous ice layer in each hole by plotting the value measured before recording the image with the value experimentally measured from the image recorded on film. There is an approximately linear correlation between these two sets of numbers, suggesting that it should be possible, at least in principle, to select holes based on the optical density measured in the low magnification search mode.

Figure 7A:
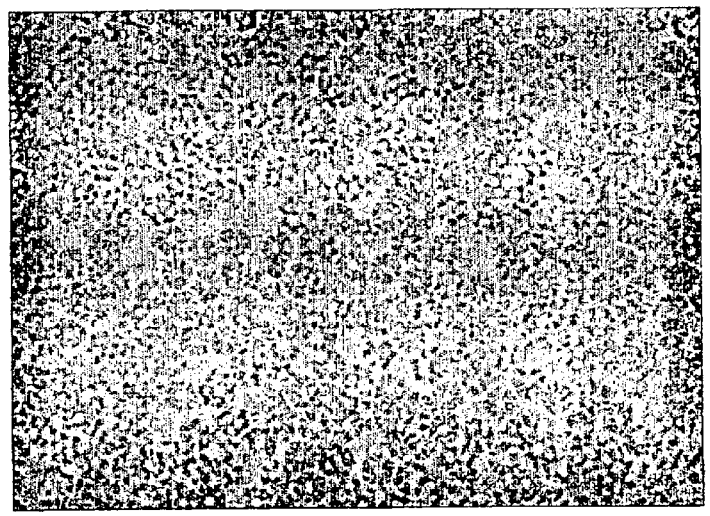
FIG. 7A is an example of an automatically recorded image; 7B is a comparison of images taken automatically (left) and manually (right).
Figure 7B:
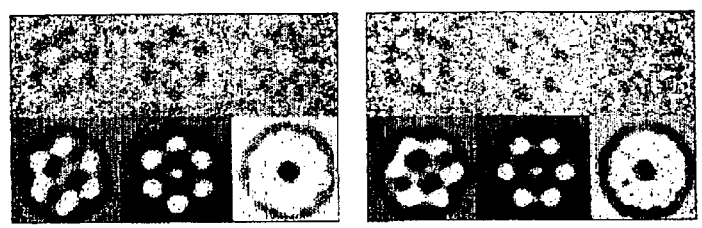

FIG. 7 shows a comparison of image quality between images recorded by a human operator and the fully automated method represented by the code given above. FIG. 7A shows a cryo electron micrograph of PDH E2CD taken at 52,000× magnification using the fully automated portion of the code above imaged with a Philips Tecnai 12 microscope. FIG. 7B shows filtered images and class averaged images of three different views of E2CD molecules from data collected manually (right) and automatically using the fully automated portion of the code above (left).

The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. An automated method for the structural determination of a sample using electron microscopy, said method comprising the steps of:
   (a) defining one or more imaging parameters;
   (b) selecting one or more sample sites for imaging based upon said imaging parameters; and
   (c) imaging said one or more sample sites;
   (d) additionally comprising the step of preparing said sample in a liquid medium, of freezing said sample and said liquid medium, wherein the frozen thickness of said sample comprises an imaging parameter.

2. The method of claim 1, wherein said imaging parameters comprise the chemical composition of said sample.

3. The method of claim 1, wherein said imaging parameters comprise the buffer conditions at sample preparation.

4. The method of claim 1, wherein the sample is frozen using ethane.

5. The method of claim 1, wherein said sample is frozen to a temperature of at least about −170° C.

6. The method of claim 1, wherein more than one sample site is imaged.

7. The method of claim 6, wherein said samples are identified by the electron microscope which undertakes a patterned search routine.

8. The method of claim 7, wherein said search routine pattern is spiral.

9. An automated method for the structural determination of a sample using electron microscopy, said method comprising the steps of:
- (a) setting imaging parameters;
- (b) setting operating conditions of said microscope wherein said operating conditions are set based on said imaging parameters, and wherein said microscope comprises an electron beam and a microscope stage;
- (c) locating at least one specific sample site to image;
- (d) adjusting focus settings;
- (e) centering said electron beam within said sample site; and
- (f) taking a picture;
- (g) wherein said sample comprises a frozen solution and wherein said imaging parameters comprise the thickness of said frozen sample.

10. The method of claim 9, wherein said step of locating at least one sample site to image further comprises the step of sending said microscope stage to a specific location.

11. The method of claim 10, wherein said step of locating at least one sample site to image further comprises the step of irradiating a portion of said frozen sample log enough to melt a portion of said frozen sample.

12. The method of claim 11, wherein said step of locating at least one sample site to image further comprises the step of estimating the thickness of said frozen sample at said sample site.

13. The method of claim 9, wherein said step of taking a picture comprises taking a picture on a charge coupled device camera.

14. The method of claim 9, wherein said step of taking a picture comprises taking a picture on photographic film.

15. The method of claim 9, wherein said step of locating at least one sample site to image further comprises the step of allowing users to store x,y locations of regions suitable for imaging.

* * * * *

UNITED STATES PATENT AND TRADEMARK OFFICE
CERTIFICATE OF CORRECTION

PATENT NO. : 6,987,266 B2
APPLICATION NO. : 10/475821
DATED : January 17, 2006
INVENTOR(S) : Subramaniam It is certified that error appears in the above-identified patent and that said Letters Patent is hereby corrected as shown below:

Title page, (57) Abstract, line 2: "Methods use in the" should read --Methods used in the--

Col. 3, line 53: "5B are a graphical" should read --5B are graphical--

Col. 10, line 14: "apart Wart number" should read --apart (part number--

Col. 32, line 19: "Example 6" should read --Example 7--

Signed and Sealed this

Eleventh Day of July, 2006

JON W. DUDAS
*Director of the United States Patent and Trademark Office*